United States Patent
Nishikawa et al.

(10) Patent No.: US 6,315,738 B1
(45) Date of Patent: Nov. 13, 2001

(54) ASSEMBLY HAVING LANCET AND MEANS FOR COLLECTING AND DETECTING BODY FLUID

(75) Inventors: Hisao Nishikawa; Kouichi Sonoda; Masao Takinami, all of Kanagawa; Naoki Morikawa, Yamanashi, all of (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/475,125

(22) Filed: Dec. 30, 1999

(30) Foreign Application Priority Data

| Jan. 4, 1999 | (JP) | 11-000215 |
| Mar. 10, 1999 | (JP) | 11-063905 |
| Jul. 7, 1999 | (JP) | 11-193754 |
| Jul. 12, 1999 | (JP) | 11-196829 |
| Nov. 12, 1999 | (JP) | 11-322465 |

(51) Int. Cl.$^7$ ............................................. A61B 5/00
(52) U.S. Cl. ........................... 600/583; 600/584; 606/181
(58) Field of Search ......................... 600/573, 576, 600/578, 579, 583, 584; 606/181, 182

(56) References Cited

U.S. PATENT DOCUMENTS

| 4,637,403 | * | 1/1987 | Garcia et al. ...................... 600/583 |
| 4,787,398 | | 11/1988 | Garcia et al. ...................... 600/583 |
| 4,790,979 | * | 12/1988 | Terminiello et al. ................ 422/56 |
| 5,029,583 | * | 7/1991 | Meserol et al. ..................... 600/316 |
| 5,279,294 | | 1/1994 | Anderson et al. .................. 600/322 |
| 5,628,764 | * | 5/1997 | Schraga .............................. 606/182 |
| 5,682,233 | * | 10/1997 | Brinda ................................ 356/246 |
| 5,700,695 | * | 12/1997 | Yassinzadeh et al. ............. 436/180 |
| 5,879,310 | * | 3/1999 | Sopp et al. ........................ 600/578 |
| 5,951,492 | * | 9/1999 | Douglas et al. .................... 600/583 |
| 5,971,941 | * | 10/1999 | Simons et al. ..................... 600/573 |
| 6,071,251 | * | 6/2000 | Cunningham et al. ............ 600/584 |

FOREIGN PATENT DOCUMENTS

| 6-339473 | 12/1994 | (JP) . |
| 7-55801 | 3/1995 | (JP) . |
| 8-247946 | 9/1996 | (JP) . |
| 9-276235 | 10/1997 | (JP) . |

* cited by examiner

*Primary Examiner*—Robert L. Nasser
*Assistant Examiner*—Charles Marmor, II
(74) *Attorney, Agent, or Firm*—Burns, Doane, Swecker & Mathis, LLP

(57) ABSTRACT

An assembly to be detachably mounted on a body fluid monitoring system is provided. The assembly has a lancet and a device for collecting and detecting a body fluid. The lancet has a puncture needle. In this assembly, the puncture needle is maintained in sterilized conditions until its use, and the sterilization can be conducted with no adverse effects on the detection device. A readily sterilizable lancet unit and a body fluid-collecting and detecting unit adapted for use in such an assembly as well as a body fluid-monitoring system including such an assembly are also provided. The assembly comprises a first housing having a sleeve which movably accommodates the lancet in its interior, and a second housing having the body fluid detection device. The first housing and the second housing share an opening. The lancet is sterilized before the assembly. The body fluid-collecting and detecting section has a body fluid guide on the periphery of the inlet.

21 Claims, 11 Drawing Sheets

FIG. 7
FIG. 8
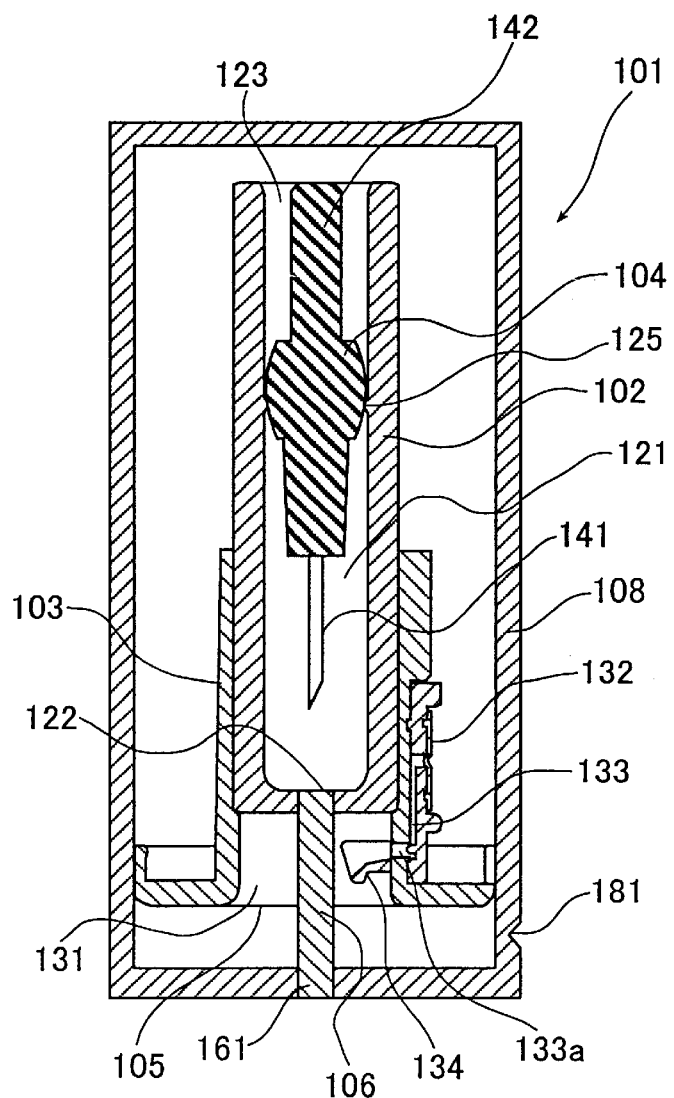
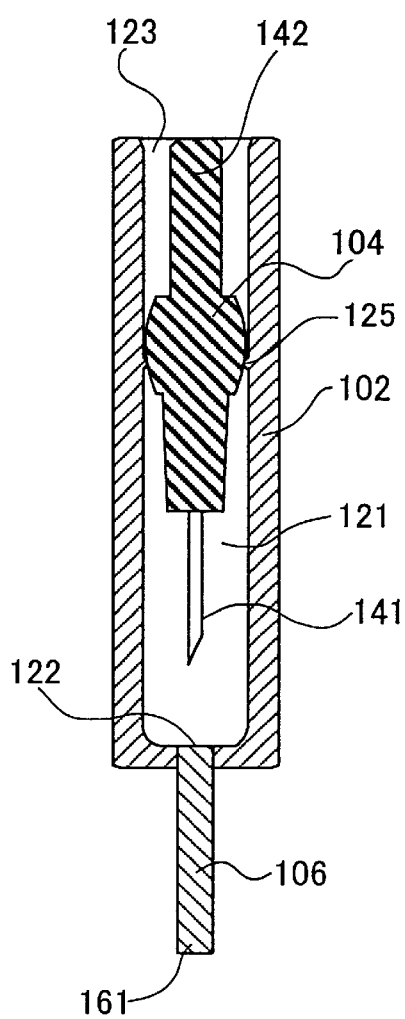

ASSEMBLY HAVING LANCET AND MEANS FOR COLLECTING AND DETECTING BODY FLUID

BACKGROUND OF THE INVENTION

This invention relates to an assembly which is detachably mounted to a body fluid-monitoring system for laboratory testing of a body fluid such as blood, wherein the assembly has a lancet and a means for collecting and detecting the body fluid. This invention also relates to a body fluid-collecting and detecting unit for use in such assembly, and a body fluid-monitoring system having such an assembly detachably mounted thereto.

With the increase in the number of patients suffering from diabetes, self-monitoring of blood glucose wherein the patient can daily monitor his or her blood glucose level has been highly recommended. In view of such situation, various systems wherein a lancet and a glucose meter are integrated have been disclosed for ease of the blood glucose self-monitoring and to enable hygienic measurement. Such systems are disclosed, for example, in JP-A 6-339473, JP-A 9-276235, and U.S. Pat. No. 4,787,398.

In the system of the type disclosed in JP-A 6-339473, the lancet mechanism and the detection mechanism are separate, and the lancet unit including the puncture needle and the detection unit including the test strip should be separately mounted on the monitoring system, and the operation is cumbersome.

JP-A 9-276235 and U.S. Pat. No. 4,787,398 proposes a body fluid-monitoring system wherein the lancet mechanism and the detection mechanism are integrally assembled.

The blood glucose meter disclosed in JP-A 9-276235 comprises a lancet, a tourniquet for compressing the finger, and a means for detecting the target component in the blood and displaying the results, accommodated in a housing. In this glucose meter, collection of the required amount of the blood is enabled by the use of the tourniquet, and as a consequence, this system is associated with the risk of infection by the blood that adheres to the tourniquet when the finger is pulled out through the tourniquet after the blood collection.

JP-A 9-276235 also discloses use of a disposable cartridge wherein a puncture needle and an electrode coated with an enzyme ink are accommodated. JP-A 9-276235, however, is silent about sterilization of the puncture needle before its use. In JP-A 9-276235, the puncture needle and the electrode coated with the enzyme ink are arranged adjacent to each other, and sterilization of the puncture needle should be quite difficult once the cartridge is accommodated in the cartridge. Assembly of the cartridge after sterilizing the puncture needle, on the other hand, is quite nonproductive since a clean room is required for such operation.

U.S. Pat. No. 4,787,398 proposes a monitoring system wherein a unit provided with a lancet having a puncture needle and a detection means having a test strip can be mounted on the main body of the monitoring system, and wherein the operation is thereby simplified. This system also suffers from the difficulty of sterilization as in the case of JP-A 9-276235, and sterilization of the unit before its use is associated with the risk of denaturing of the reagents immobilized on the test strip. Therefore, it has been difficult to deliver a product wherein sterilization of the puncture needle is maintained until the use of the product.

The self-monitoring of blood glucose is normally conducted by using a lancet and a glucose meter. To be more specific, the lancet having a puncture needle or a blade on its tip is first used to collect the blood of required volume by pricking the finger tip with the lancet and milking or squeezing the skin around the puncture site to ensure the formation of the blood droplet of required amount. The lancet is held by the hand which is not bleeding in the step of blood collection. The lancet is then replaced with the glucose meter for the measurement of the blood glucose. Such change of the device should be conducted while the blood is flowing out from the punctured site, and this procedure is associated not only with inconvenience of the operation but also with unfavorable sanitary conditions.

Use of a body fluid-collecting cartridge is also proposed including the type wherein the blood is dropped on the test strip in the cartridge, the type wherein the blood is guided to the test strip by capillary action, and the type wherein the blood is once introduced into a reservoir defined in the cartridge and then guided to the test strip by capillary action. See, for example, JP-A 4-264246, JP-A 7-55801 and JP-A 247946.

The type wherein the blood is dropped on the test strip in the cartridge is associated with the problem of inconsistent measurement value since the time interval between the blood collection and mounting of the cartridge is not constant.

The type wherein the blood is guided to the test strip by capillary action is also associated with various demerits. For the purpose of reducing the burden of the patient, the interior volume of the capillary is minimized to reduce the amount of the blood remaining in the capillary after the detection. Such reduction in the volume of the capillary results in the reduced size of the inlet of the capillary, and introduction into the capillary of the blood becomes difficult. In addition, when the area surrounding the capillary inlet erroneously becomes in contact with the blood, sucking of the blood into the capillary is impeded. The situation is the same even if a reservoir is provided in the cartridge unless an appropriate guiding structure is provided in the area surrounding the inlet. Moreover, when such reservoir is in the same plane as the main body of the cartridge, there is always some risk of blood leakage from the gap between the finger and the reservoir due to the finger print unless the finger is very tightly pressed against the cartridge, and such blood leakage is likely to result in the blood adhesion to the back surface of the cartridge, and also, increase in the amount of the blood necessary for the measurement. On the other hand, when the blood volume collected by the lancet is insufficient, the blood will never reach the test strip. The measurement is, therefore, unreliable and unsanitary.

In view of such situation, there is a strong demand for a body fluid-collecting cartridge which is capable of reliably sucking the collected body fluid into its interior with no adhesion on the exterior surface, and wherein collection of minimum necessary amount of the body fluid is required.

SUMMARY OF THE INVENTION

An object of the present invention is to provide an assembly which is detachably mounted on a body fluid-monitoring system wherein lancing mechanism and measuring mechanism are assembled in one assembly, and which comprises the lancing section including the puncture needle and the detection section including the test strip.

Another object of the invention is to provide an assembly wherein the lancet is maintained in sterilized conditions until its use while function of the detection section including the test strip is maintained.

A further object of the present invention is to provide a body fluid-collecting and detecting unit for use in such assembly, and a body fluid-monitoring system having such an assembly detachably mounted thereto.

This and other objects of the present invention will be apparent by reading the following description in conjunction with the drawings.

Such objects are attained by the present invention as summarized below in (1) to (26).

(1) An assembly having a lancet and a means for collecting and detecting a body fluid wherein said assembly is to be detachably mounted on a body fluid-monitoring system having a lancing means and said assembly comprises:

a lancet section comprising a lancet having a puncture needle on its distal end and a connector on its proximal end for connection to said lancing means of the body fluid-monitoring system, and a first housing having a sleeve which movably accommodates said lancet in its interior, and which has a first opening on its distal end to enable projection of the needle into its exterior and a proximal opening to enable connection of said connector with said lancing means of the body fluid-monitoring system, and wherein said lancet before the lancing is secured in said sleeve at a position near its proximal opening capable to gas-tightly seal said sleeve;

a body fluid-collecting and detecting section comprising a body fluid detection means and a second housing having a second opening for introducing the body fluid into said detection means;

a first seal member for sealing said first opening and optionally a second seal member for sealing said proximal opening; and wherein said first housing is gas-tightly sealed with both said first seal member for sealing said first opening and said lancet or said optional second seal member for sealing said proximal opening; and said first housing and said second housing are fixedly integrated each other such that said first opening of said first housing and said second opening of said second housing together define a distal opening to enable the projection of said puncture needle to the exterior of said assembly, and the one-piece assembly having the lancet section and the body fluid-collecting and detecting section is thereby constituted.

(2) An assembly according to the above (1) produced by sterilizing said lancet section having said puncture needle accommodated in said first housing with said first opening and said proximal opening sealed; and assembling the sterilized lancet section with said body fluid-collecting and detecting section in one piece unit.

(3) An assembly according to the above (1) wherein the entire assembly after assembling is covered with a protective shield.

(4) An assembly according to the above (2) wherein the entire assembly after assembling is covered with a protective shield.

(5) An assembly according to the above (3) or (4) wherein said first seal member is connected to said protective shield and said first seal member is removed from said first opening simultaneously with the removal of said protective shield.

(6) An assembly according to any one of the above (2) to (5) wherein said puncture needle remains sterilized until said first seal member is removed from said first opening.

(7) An assembly according to any one of the above (1) to (6) wherein said first housing has a means for preventing detachment of said lancet after its use.

(8) An assembly according to the above (7) wherein said detachment-preventing means also serves the function of sealing said proximal opening of said sleeve.

(9) An assembly according to any one of the above (1) to (8) wherein said second housing is defined with a flow path for guiding the body fluid from said distal opening to said body fluid detection means by capillary action, and an inlet port for guiding said body fluid into said flow path. An assembly according to any one of the above (1) to (9) wherein said flow path may have an air vent near said body fluid detection means.

(10) An assembly according to the above (9) wherein said flow path in the second housing comprises a plurality of flow path sections between which corners are defined at an angle, and a projection protruding into the flow path is provided on each corner so that the tip of the projection contacts with meniscus of the body fluid formed at the corner.

(11) An assembly according to the above (9) or (10) wherein said inlet port has a body fluid guide formed along its periphery.

(12) An assembly according to the above (11) wherein said body fluid guide comprises two or more guide members and said guide members are projections formed on the periphery of said inlet port.

(13) An assembly according to the above (11) or (12) wherein said body fluid guide is located inside of said second opening.

(14) An assembly according to any one of the above (11) to (13) wherein said body fluid guide has a constitution comprising two side members and a lower plate member.

(15) An assembly according to the above (14) wherein said lower plate member has a downwardly extending projection on a distal section thereof.

(16) An assembly according to the above (14) or (15) wherein said body fluid guide members are designed such that the width between said side members increases from the side of said inlet to the side of distal end, and surface tension of said body fluid is lower in the interior space enclosed with said fluid guide members than in the interior of said flow path, and the distal ends of said side members are mounted at an angle less than 90° to the bottom face of said second opening.

(17) An assembly according to any one of the above (1) to (16) wherein said second housing has a sleeve in its interior to fittingly receive at least a part of the sleeve of the first housing, and said sleeve of the second housing has an opening in its body; and detection area of the body fluid detection means is secured to the exterior surface of said sleeve of the second housing.

(18) An assembly according to any one of the above (11) to (17) wherein said puncture needle passes near the tip of said body fluid guide or between side members of said body fluid guide during the puncture.

(19) An assembly having a lancet assembled with a body fluid-collecting and detecting section, wherein said lancet has a puncture needle on its distal end and a connector on its proximal end for connection to the lancing means of the body fluid-monitoring system, and said lancet section has been gas-tightly sealed under sterilized conditions.

(20) A body fluid-collecting and detecting unit comprising:

an inlet port for the body fluid;

a test strip which enables measurement of the target component in the body fluid;

a flow path for guiding the body fluid from said inlet port to said test strip by capillary action; and a body fluid guide formed along the periphery of the inlet port.

(21) A body fluid-collecting and detecting unit according to claim 20 wherein said body fluid guide comprises two or more guide members and said guide members are projections formed on the periphery of said inlet port.

(22) A body fluid-collecting and detecting unit according to the above (20) or (21) wherein said body fluid-collecting and detecting unit is accommodated within a housing having an opening, and said body fluid guide is accommodated inside said opening.

(23) A body fluid-collecting and detecting unit according to any one of the above (20) to (22) wherein said body fluid guide has a constitution comprising two side members and a lower plate member.

(24) A body fluid-collecting and detecting unit according to the above (23) wherein said lower plate member has a downwardly extending projection on a distal section thereof.

(25) A body fluid-collecting and detecting unit according to the above (23) or (24) wherein said body fluid guide members are designed such that the width between said side members increases from the side of said inlet to the side of distal end, and surface tension of said body fluid is lower in the interior space enclosed with said fluid guide members than in the interior of said flow path, and the distal ends of said side members are mounted at an angle less than 90° to the bottom face of said second opening.

(26) A body fluid-monitoring system comprising a main body of the body fluid-monitoring system and the assembly of any one of the above (1) to (19), wherein said main body includes:

a lancing means having a recess at its distal end, a means for measuring the target component in the body fluid, and a holder means for detachably holding the assembled housings of the assembly, and said assembly is held by said holder means, and the connector of said lancet is fitted into said recess formed in the distal end of said lancing means.

BRIEF DESCRIPTION OF THE DRAWINGS

FIG. 7 is a lateral cross sectional view of the assembly 101 according to the second embodiment of the present invention.

FIG. 8 is a lateral cross sectional view similar to FIG. 1 partially showing the first housing 102.

FIG. 19 is a plan view showing an embodiment wherein the body fluid guide 34 covers three directions (i.e. downward, left and right directions) of the body fluid inlet 33a.

PREFERRED EMBODIMENTS OF THE INVENTION

Figure 1:
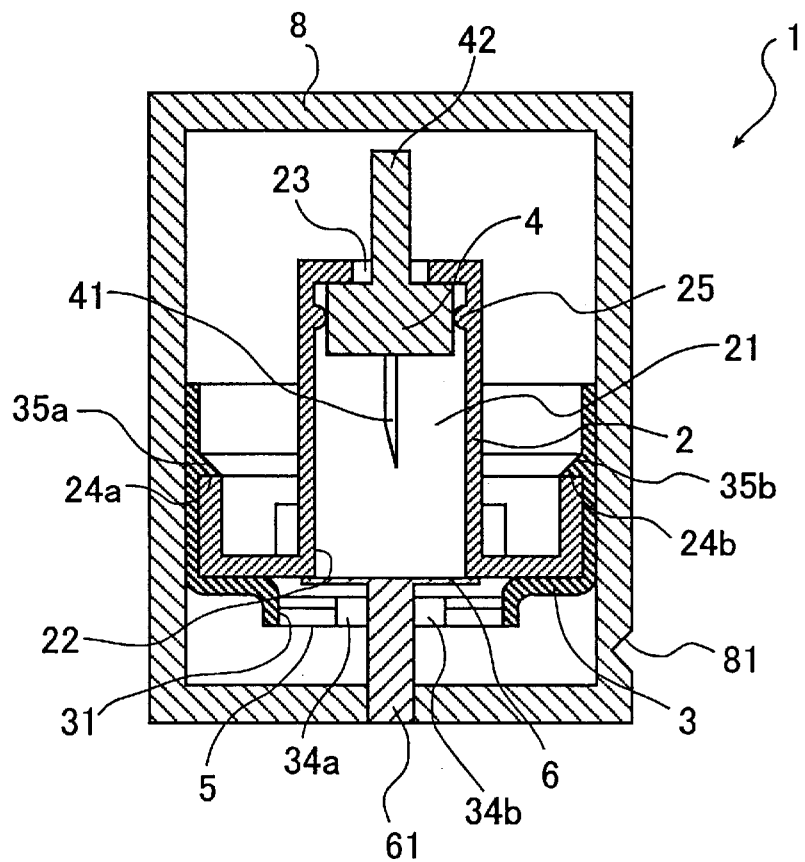
FIG. 1 is a lateral cross sectional view of the assembly 1 according to first embodiment of the present invention.

This invention provides an assembly to be detachably mounted on a body fluid-monitoring system, and the assembly is provided with a lancet and a means for collecting and detecting a body fluid.

The assembly comprises a lancet section, a body fluid-collecting and detecting section, and a first seal member.

The lancet section comprises a lancet and a first housing. The lancet has a puncture needle on its distal end a connector on its proximal end for connection to a lancing means in the body fluid-monitoring system. The first housing has a sleeve which movably accommodates the lancet in its interior. The sleeve has a first opening on its distal end to extend the needle to the exterior of the sleeve and a proximal opening to enable the connector to connect with the lancing means in the body fluid-monitoring system. The lancet before the lancing is secured in the sleeve at a position near its proximal opening to gas-tightly seal the sleeve. The body fluid-collecting and detecting section comprises a body fluid detection means and a second housing having a second opening for introducing the body fluid into said detection means. The first seal member seals the first opening.

In the assembly of the present invention, the first housing and the second housing are fixedly secured to each other such that the first opening of the first housing and the second opening of the second housing define a distal opening to enable the puncture needle to extend beyond the opening, and the one-piece assembly having the lancet section and the body fluid-collecting and detecting section is thereby constituted.

As described above, in the assembly of the present invention, the lancet unit in the first housing and the body fluid-collecting and detecting unit in the second housing are joined in one unit to share their opening. The puncture needle of such lancet unit can be sterilized in the first housing with the first opening and the proximal opening closed.

Accordingly, the present invention also provides a sterilized lancet unit to be assembled with the body fluid-collecting and detecting unit, and a body fluid-collecting and detecting unit to be assembled with the sterilized lancet unit.

Next, the first preferred embodiment of the present invention is described in detail by referring to the drawings (mainly FIGS. 1 to 6). It should be noted that, in the drawings, the same reference numeral indicates equivalent members, and description may be omitted for such equivalent members.

FIG. 1 is a lateral cross sectional view of an assembly 1 according to the first embodiment of the present invention.

The assembly 1 comprises a first housing 2 accommodating the lancet 4 and a housing 3 accommodating the body fluid-collecting and detecting means.

Figure 2:
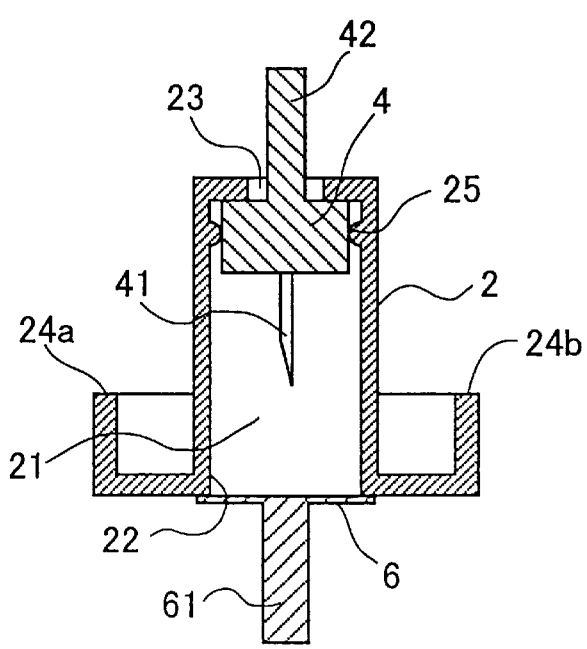
FIG. 2 is a lateral cross sectional view similar to FIG. 1 partially showing the first housing 2.

FIG. 2 is a cross sectional view of the lancet section of FIG. 1. The first housing 2 has a sleeve 21 in which the lancet 4 is movably accommodated. The sleeve 21 has a first opening 22 at its distal end and a proximal opening 23 at its proximal end.

Figure 3:
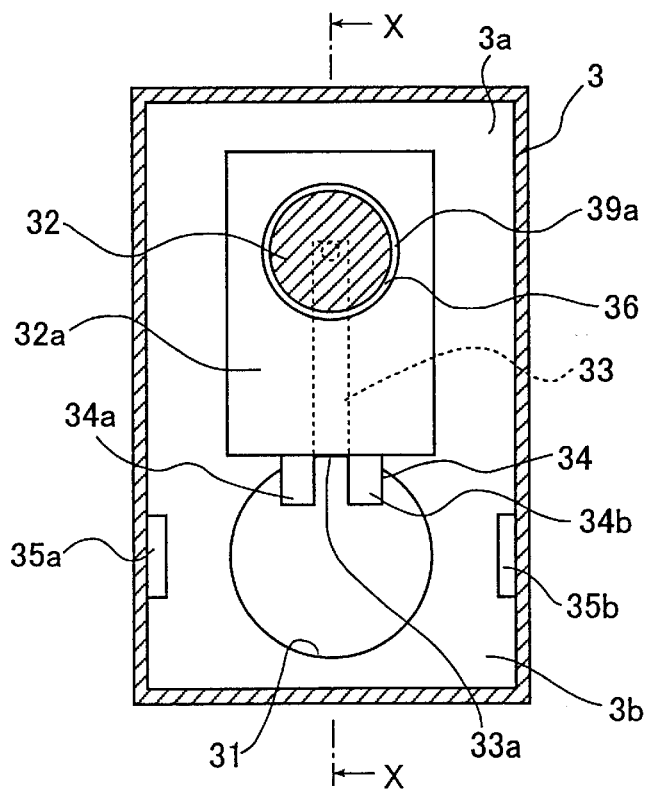
FIG. 3 is a plan view of the second housing 3.

FIG. 3 is a plan view of the body fluid-collecting and detecting section, and this section comprises detection means 32 and the housing 3 having a second opening 31 formed therewith to allow introduction of the body fluid to the detection means 32.

Figure 4:
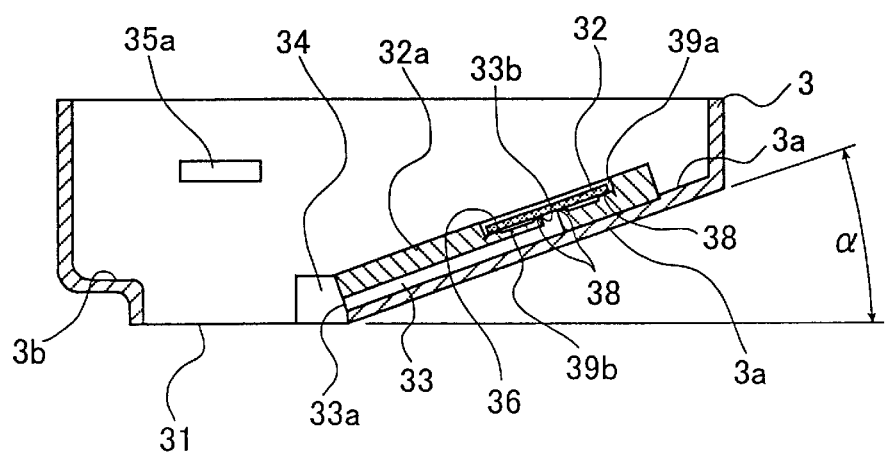
FIG. 4 is a cross sectional view taken along lines X—X of the second housing 3 in FIG. 3.

FIG. 4 is a cross sectional view taken along lines X—X of the second housing 3 in FIG. 3.

The first housing 2 and the second housing 3 are fixedly secured to each other to constitute the assembly 1 such that the first opening 22 and the second opening 31 surrounding the first opening 22 together form the distal opening 5.

Figure 6:
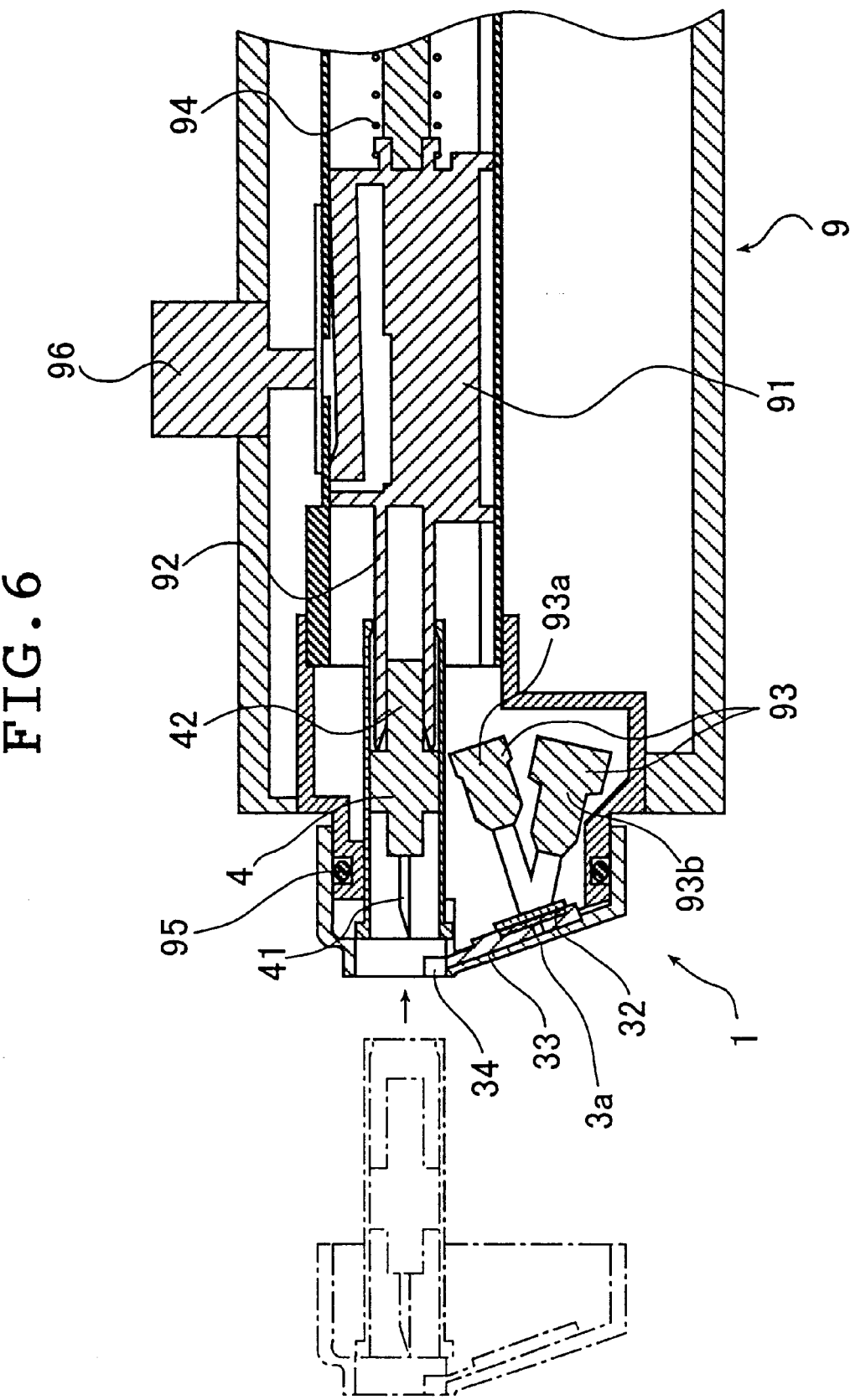
FIG. 6 is a lateral cross sectional view of the assembly 1 according to the first embodiment of the present invention showing how it is used.

FIG. 6 is a view showing the assembly 1 mounted on a body fluid-monitoring system 9.

The second housing 3 is not limited for its shape as long as it has the detection means 32 defined therein; it shares its opening 31 with the first housing 2 to form the distal opening 5; and it is capable of holding the first housing 2 in its interior.

In the first embodiment, the detection means 32 is formed at a particular angle in relation to the axial direction of the member holding the sleeve 21 of the housing 2.

The first housing 2 has the sleeve 21 in its interior, and the lancet 4 is movably accommodated in the sleeve 21.

The sleeve 21 is not limited for its shape, and it may be either a cylinder or a rectangular tube. For structural easiness of production, the sleeve 21 is preferably a cylinder.

The lancet 4 has a puncture needle 41 at the distal end, and a connector 42 at the proximal end for connection to a lancing means 91 in the body fluid-monitoring system 9. The shape of the connector 42 is not limited to the convex type as shown in the drawings, and the connector 42 of any shape may be employed as long as it corresponds to the shape of the lancing means 91. In addition, the connector 42 may not necessary extend beyond the proximal opening 23.

The lancet 4 is secured at a position near the proximal end of the sleeve 21, namely, at a position such that the puncture needle 41 does not extend beyond the first opening 22. The lancet 4 is secured to the sleeve 21 at a firmness such that the puncture needle 41 does not extend beyond the first opening 22 before the use, such that the operation of connecting the connector 42 with the lancing means 91 can be accomplished, and such that the connector 42 is released from the secured position when the lancet 4 is urged by the pushing force of the lancing means 91 upon its use. The means for securing the lancet 4 is not limited, and the lancet 4 may be secured by providing an engagement means on the interior surface of the sleeve 21 and/or on the exterior surface of the lancet 4; by utilizing the friction between the interior surface of the sleeve 21 and the exterior surface of the lancet 4; or by weakly bonding the contact surfaces with an adhesive or by fusion.

The lancet securing means may also serve the function of the mechanism for preventing detachment of the lancet 4 as well as the mechanism of sealing the proximal opening 22. As will be described later, the lancet detachment-preventing mechanism ensures safe disposal of the assembly after its use with no risk of prickling the skin with the puncture needle 41 which has accidentally extended into the exterior of the sleeve. To be more specific, upon detachment of the assembly 1 from the main body of the body fluid-monitoring system 9, the lancet 4 is pulled back in the direction toward its proximal end to be secured in the lancet securing means since the connector 42 is fittingly secured in the recess 92 at the distal end of the lancing means 91. The seal mechanism of the proximal opening 22 prevents interior of the sleeve from contamination by bacteria and other microorganisms.

In such a case, the lancet 4 before its use is secured at a position near the proximal opening 23 such that the proximal opening 23 is sealed by the lancet 4. Such sealing of the proximal opening 23 may be accomplished by the same method as described for the securing of the lancet 4, and in a typical embodiment, the lancet 4 is fitted into the space defined by a ridge 25 extending in circumferential direction on the interior surface of the sleeve 21 as shown in FIGS. 1 and 2. Alternatively, the interior of the sleeve 21 may be narrowed near its proximal end and the lancet 4 may be fittingly secured in such narrow proximal end of the sleeve 21, or the lancet 4 may be fitted into the space between the protrusions provided in some part of the interior surface of the sleeve 21 to facilitate gas-tight contact between the interior surface of the sleeve 21 near its proximal end and the exterior surface of the lancet 4 near its proximal end.

When the assembly 1 is detached from the body fluid-monitoring system 9, the lancet will be pulled back toward the proximal end of the first housing 2 since the lancet 4 is connected to the lancing means 91 of the body fluid-monitoring system 9 through the connector 42. When the lancet 4 has been fittingly secured to the securing/sealing means as described above such as the ridge 25 extending in circumferential direction, the connector 42 becomes detached from the lancing means 91, and the assembly 1 will be finally detached from the body fluid-monitoring system 9. In the course of the detachment, the puncture needle 41 becomes firmly secured to the sleeve 21, and the puncture needle 41 is reliably prevented from extending beyond the second opening 31. Accidental prickling of the skin by the puncture needle 41 after its use is thereby prevented.

As described above, the gas-tight sealing of the sleeve 21 at the proximal opening 23 is preferably realized by the gas-tight sealing by the lancet 4. Alternatively, the proximal opening 23 may be sealed by a second seal member (not shown) like the first seal member 6 as will be described later. In such a case, the proximal opening 23 may or may not be sealed by the lancet 4.

When the proximal opening 23 of the sleeve 21 is sealed by the lancet 4, the lancet 4 must fit in the sleeve 21 near its proximal end, and therefore, the lancet 4 should have a cross section that corresponds to the cross section of the sleeve 21. In principle, the lancet 4 may be formed from the same material as the first housing 2 or the second housing 3 as will be described below, and the material used for the lancet 4 may preferably have some degree of flexibility.

Exemplary materials used for the first housing 2 include ABS, polyethylene, polypropylene, polystyrene, polyvinyl chloride, polyvinylidene chloride resin, polyphenylene oxide, thermoplastic polyurethane, polymethylene methacrylate, polyoxyethylene, fluororesin, polycarbonate, polyamide, acetal resin, acryl resin, polyethylene phthalate and other thermoplastic resins used in the injection molding; and phenol resin, epoxy resin, silicone resin, unsaturated polyester resin and other thermosetting resins.

The interior of the sleeve 21 is kept in gas-tightly sealed conditions by sealing the first opening 22 and the proximal opening 23. The first opening 22 is sealed by the first seal member 6. As shown in the drawings, the first seal member 6 is in the form of a film secured to the periphery of the first opening 22 with an adhesive or by fusion.

Although the first seal member 6 is preferably in the form of a film for ease of bonding by adhesion or fusion as well as peeling, the first seal member 6 may also be in the form of a lid or a plug as shown in FIG. 8.

The interior of the first housing 2 is maintained in sterilized condition by sterilizing the sleeve 21 after enclosing the lancet 4 in its interior and sealing the proximal opening 23; or enclosing the sterilized lancet 4 in the interior of the sterilized sleeve 21 and maintaining the interior of the sleeve 21 in sealed conditions until its use. Of these procedures, sterilization of the sleeve 21 after enclosing the lancet 4 and sealing the proximal opening 23 is advantageous for ease of the operation.

The sterilization may be conducted by any method, for example, by sterilization with EOG, γ ray, electron beam, or the like.

As described above, the first housing 2 is assembled with the second housing 3 to produce the assembly 1 after ensuring that the sterility of the interior of the sleeve 21 will be maintained until its use.

Figure 5:
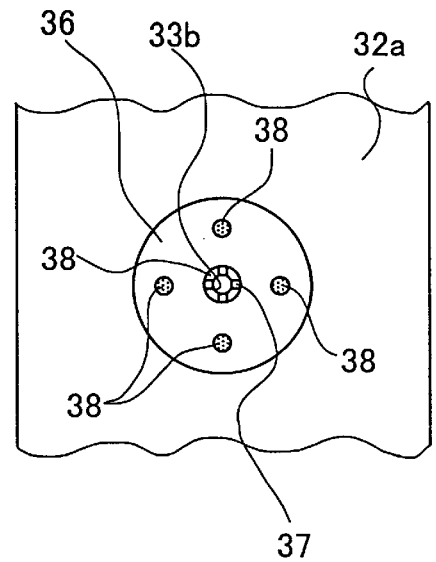
FIG. 5 is a plan view of the test strip holder 36 (without paper) in the second housing 3.

Next, the body fluid-collecting and detecting section is described by mainly referring to FIGS. 3 to 5.

The body fluid-collecting and detecting section accommodates the body fluid detection means 32 in its interior, and comprises the second housing 3 having a second opening 31 for introducing the body fluid into the detection means 32.

In the present embodiment, the second opening 31 is formed in the bottom surface 3a of the second housing 3 at an eccentric position. The wall of the housing 3 on the side of the second inlet 31 has a shoulder 3b for holding at least a part of the first housing 2. A test strip housing 32a is provided on the bottom surface 3a of the housing 3 on the side different from the second opening 31.

In FIGS. 3 and 4, a test strip is used in the body fluid detection means 32. The test strip (body fluid detection means) 32 is secured in the test strip holder 36 formed as a recess in the test strip housing 32a. A body fluid inlet 33a and a flow path 33 for guiding the body fluid from the body fluid inlet 33a to the test strip 32 are formed between the test strip housing 32a and the wall of the second housing 3. It should be noted that the body fluid detection means is not limited to the test strip, and any medium suitable as a body fluid detection means of the body fluid monitoring system 9 may be used.

The material used for the second housing 3 may be the same as the one described for the first housing 2. When the body fluid-measuring means 93 in the body fluid monitoring system 9 is an optical means which conducts the measurement by detecting the color reaction on the test strip, the housing 3 may preferably comprise a non-transparent material to thereby shut out the influence of exterior light and increase the measurement accuracy. For ease of confirming the movement of the body fluid in the flow path 33, the second housing 3 may comprise a colored, translucent resin.

The cross section and the length of the flow path 33 may vary in accordance with the amount of the body fluid required for the measurement. The flow path 33, however, is preferably designed such that the volume of the body fluid remaining in the flow path 33 is minimized. The flow path 33 may typically comprise a groove having a semi-circular, V-shaped, or rectangular cross section, and for reducing the amount of the body fluid remaining in the flow path 33, the flow path 33 may preferably comprise a shallow groove having a rectangular cross section. The depth is preferably in the range of about 0.05 to about 0.5 mm, and the width is preferably in the range of from about 0.5 to about 3 mm. The flow path 33 may preferably have a short length although the length may depend on the position of the body fluid-measuring means 93 of the body fluid monitoring system 9. The suitable length, however, is in the range of from about 5 mm to about 15 mm.

When the body fluid is introduced along the flow path 33 from the body fluid inlet 33a to the test strip 32 in a closed system, the capillary action may stop before the reaching of the body fluid to the test strip 32. In view of such situation, provision of an air vent is necessary, and the air vent is provided in the test strip holder 36.

A preferable structure of the air vent is shown in the plan view of the test strip holder 36 in FIG. 5. In this structure, the test strip supports 38 and the air vent 37 at the end 33b of the flow path 33 on the side of the test strip 32 are formed so that the test strip can be secured as shown in FIG. 4 wherein a gap 39a is defined between the periphery of the test strip 32 and the periphery of the test strip holder 36, and a gap 39b is defined between the lower surface of the test strip 32 and the test strip holder 36. The test strip 32 is supported between the test strip supports 38 and the end 33b of the flow path 33 on the side of the test strip 32. The gap 39b between the lower surface of the test strip 32 and the test strip holder 36 is preferably about 0.01 to about 0.3 mm.

Figure 13:
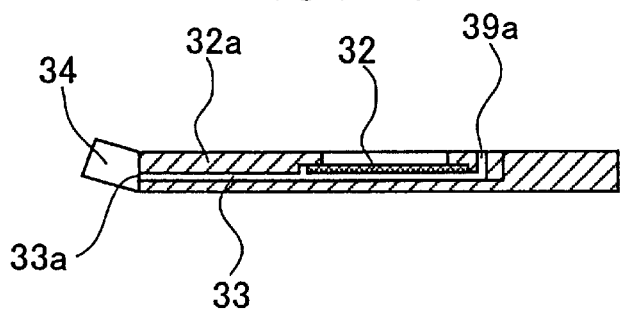
FIG. 13 is a cross sectional view of another embodiment of the air vent structure corresponding to FIG. 4.

The air vent structure is not limited to the one as described above, and the test strip 32 may be placed at some midpoint in and on one side of the flow path 33 so that an air vent 39a is formed at the end of the flow path 33 as shown in FIG. 13.

The test strip housing 32a which defines the flow path 33 may be formed from the same material as the second housing 3. The test strip housing 32a, however, is preferably formed from a material of high hydrophilicity such as acryl resin. When the test strip housing 32a is formed from a material which is not sufficiently hydrophilic, the surface of the second housing 3 may be treated to impart the surface with the hydrophilicity to improve the sucking of the body fluid into the flow path 33. Typical such treatments include physical activations such as ozone treatment, plasma treatment, glow discharge, corona discharge, UV irradiation; coating of a surfactant, water soluble silicone, hydroxypropyl cellulose, polyethylene glycol, polypropylene glycol, or the like.

The flow path 33 may be may be formed by various procedure. When the flow path 33 is defined by the test strip housing 32a and the second housing 3, the flow path 33 may be formed by injection molding the test strip housing 32a and the second housing 3 in one piece. Alternatively, the flow path 33 may be formed in the second housing 3 by cutting or pressing the housing 3, or by fixedly securing a tube or a groove-shaped member in the housing 3.

The body fluid detecting means or the test strip 32 is not limited to any particular type, and any material matching with the body fluid-measuring means 93 of the body fluid monitoring system 9 may be used. For example, when the body fluid-measuring means 93 is an optical measurement means which detects color reaction in the test strip as in the case of the measurement of glucose in blood, the test strip may be impregnated with glucose oxidase, peroxidase, and a chromogenic agent followed by drying. The test strip 32 is preferably a porous membrane in the form of a nonwoven, a woven fabric, a stretched sheet, or the like prepared from a material such as a polyester, a polyamide, a polyolefin, a polysulfone, a cellulose, or the like. Since the test strip 32 is impregnated with various reagents as well as the body fluid, the test strip 32 is preferably the one formed from a hydrophilic material or the one which has been treated to impart hydrophilicity. The test strip 32 may be either a mono-layer sheet or a multi-layer sheet.

The body fluid inlet 33a is preferably formed with a body fluid guide 34 on its periphery. The body fluid guide 34 has the function of guiding the body fluid which becomes in contact with the guide 34 to the body fluid inlet 33a.

Provision of such guide 34 enables efficient introduction of the body fluid into the flow path 33. Accordingly, the present invention also provides a body fluid-collecting and detecting unit comprising the body fluid inlet 33a, the test strip 32 which enables the measurement of the target component in the body fluid, the path 33 which sucks the body fluid from the body fluid inlet 33a to the test strip 32, and a body fluid guide 34 provided on the periphery of the body fluid inlet 33a. Also provided in the present invention is a body fluid-collecting and detecting unit wherein the components as described above are accommodated within the housing 3.

The body fluid guide 34 may be formed from the same material as the second housing 3 or the test strip housing 32a, and the body fluid guide 34 is preferably imparted with hydrophilicity as in the case of the flow path 33.

The body fluid guide 34 may be located inside of the second opening 31 of the second housing 3.

When the body fluid guide 34 has an inappropriate shape, the excess body fluid which was not sucked from the body fluid inlet 33a will spread around the second opening 31 to invite sanitary problem. The body fluid guide 34 of an inappropriate shape will also result in an insufficient sucking of the body fluid into the flow path 33, and the amount of body fluid required for the measurement will be increased to result in the increased burden of the patient. Accordingly, the body fluid guide 34 should have a structure which is capable of rapidly guiding the body fluid to the body fluid inlet 33a, and which is capable of retaining a large amount of the body fluid to prevent the spreading or flowing out of the body fluid to surrounding areas. A typical structure of the body fluid guide 34 is two or more projections formed in the periphery of the body fluid inlet 33a.

Figure 14:
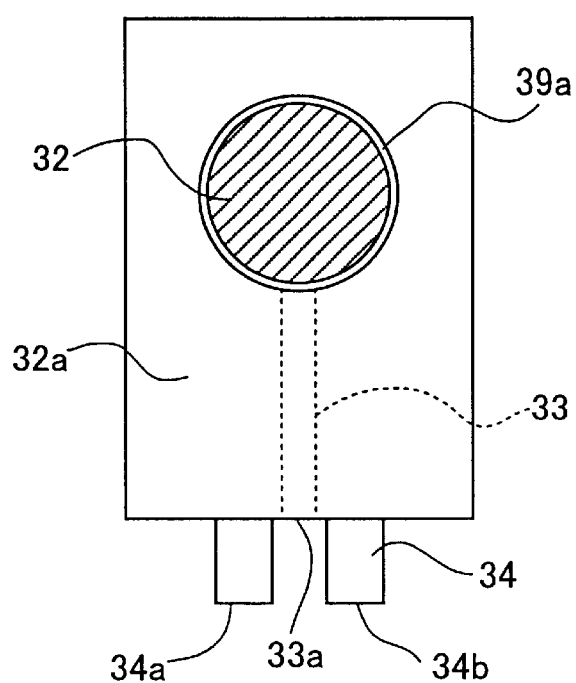
FIG. 14 is a plan view of the body fluid guide according to an embodiment of the invention.
Figure 15:
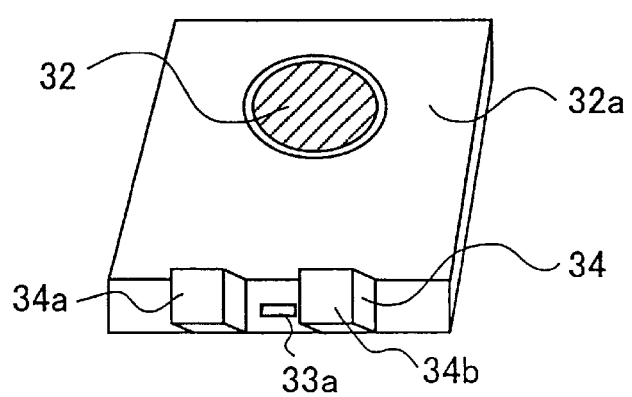
FIG. 15 is a perspective view of the body fluid guide according to the embodiment of FIG. 14.

An embodiment of the body fluid guide is shown in plan view (FIG. 14) and in perspective view (FIG. 15). The body fluid guide of this embodiment comprises guide members 34a and 34b in the form of rails provided on opposite ends and on the periphery of the body fluid inlet 33a.

The volume of the space defined by the body fluid guide 34 may vary by the volume of the body fluid collected, namely, by the diameter of the body fluid collected. The width of the guide 34 is at most the diameter of the body fluid collected. For example, when the body fluid in an amount of about 4 μl is collected as in the case of blood glucose monitoring, the body fluid emerging on the skin surface is about 3 mm in diameter, and in such a case, the guide 34 may preferably have a width of about 1 mm to about 3 mm, a height of about 0.5 mm to about 3 mm, and a length of about 1 mm to about 3 mm. The height of the guide 34a and 34b is preferably equivalent to the maximum diameter of the body fluid inlet 33a.

Figure 16:
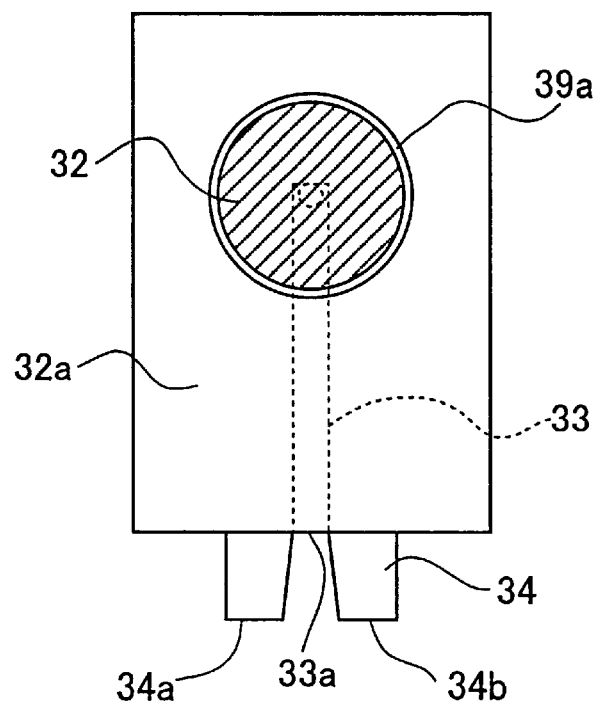
FIG. 16 is a plan view of the body fluid guide according to another embodiment.

The shape of the guide members 34a and 34b is not limited to the one shown in FIG. 14 wherein opposed interior surfaces are arranged parallel to each other. The guide members 34a and 34b may also be designed as shown in FIG. 16 wherein the space defined by the opposed interior surfaces widen toward the center of the second opening 31. In other word, the body fluid guide members are designed such that the width between said side members increases from the side of said inlet to the side of distal end.

Figure 17:
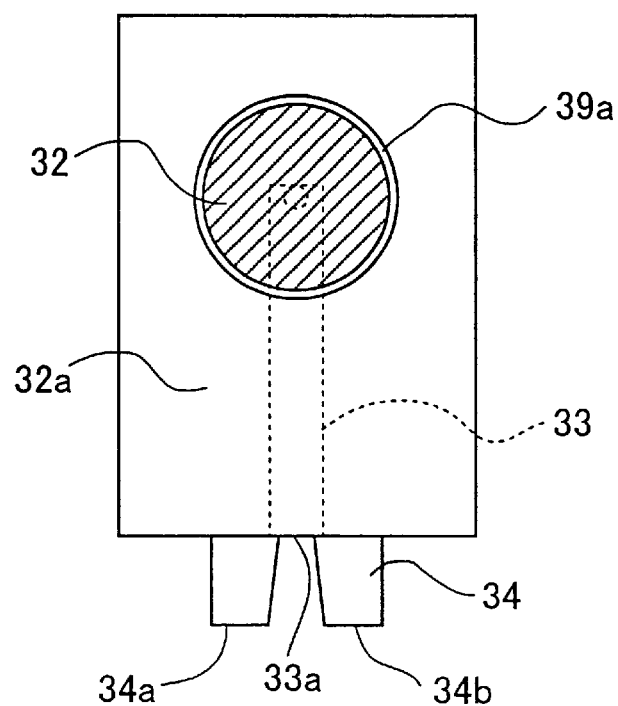
FIG. 17 is a plan view of the body fluid guide according to a further embodiment.

In addition, the guide members 34a and 34b may be arranged as shown in FIG. 17 such that the diameter defined by the opposed interior surfaces of the guide members 34a and 34b at the connection with the body fluid inlet 33a is smaller than the diameter of the body fluid inlet 33a. When the guide members 34a and 34b are designed such that the space defined by the opposed interior surfaces widen toward the center of the body fluid droplet the body fluid is smoothly fed from the skin surface into the flow path 33 since surface tension of the body fluid in the flow guide 34 is smaller than the surface tension in the flow path 33 and all the body fluid in the guide 34 will be conveyed to the body fluid inlet 33a and then to the flow path 33. As a consequence, there is no need to take the dead volume in the guide 34 into account.

The body fluid guide 34 is not limited to the embodiments comprising two guide members 34a and 34b as described above, and may comprise three or four members wherein the body fluid guide 34 covers all four directions (right, left, upward and downward directions) or three directions (right, left and downward directions) of the body fluid inlet 33a. The body fluid guide 34 may also comprise continuous members extending in circumferential direction, a semicircumferential member, a dome-shaped member, or the like.

Figure 18:
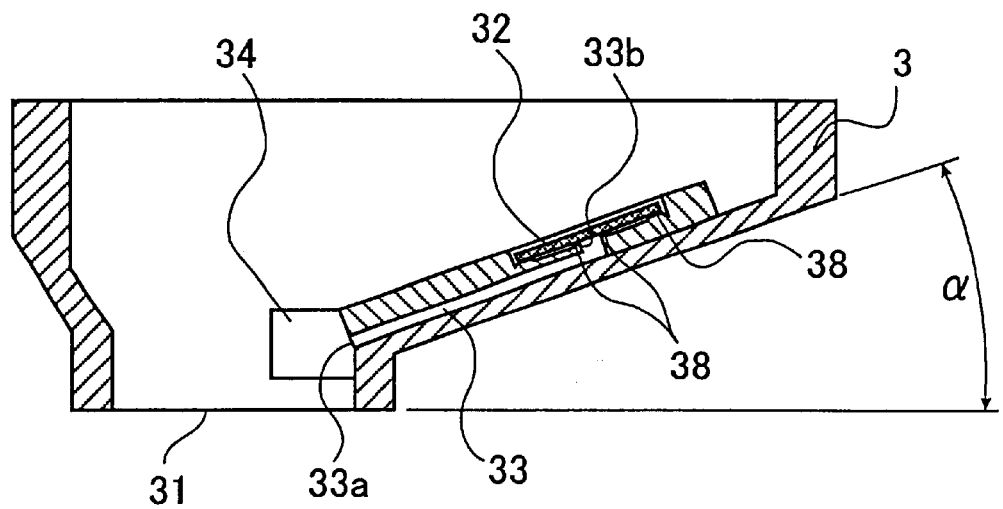
FIG. 18 is a cross sectional view of the body fluid guide according to a further embodiment.

The bottom surface of the body fluid guide 34 and the bottom surface of the second housing 3 may not necessarily define the same plane. FIG. 18 is a cross sectional view of the embodiment corresponding to the embodiment shown in FIG. 4. In this embodiment, the bottom surface of the body fluid guide 34 is beyond the bottom surface of the second housing 3.

In the preferred embodiment, the bottom surface of the body fluid guide 34 is higher than the bottom surface of the second housing 3 (the second opening 31), so that the bottom surface of the body fluid guide 34 can contact with the top surface of bulged skin when the monitoring system 9 was on the skin. In another embodiment, the bottom surface of the body fluid guide 34 may be beyond the bottom surface of the second housing 3 not to contact with the top surface of bulged skin, but to contact only with the body fluid droplet. The suitable height of bottom surface of the body fluid guide 34 from the bottom surface of the second housing 3 is in the range of from about 0.1 mm to about 5 mm, preferably from about 0.5 mm to about 1.5 mm.

Figure 19:
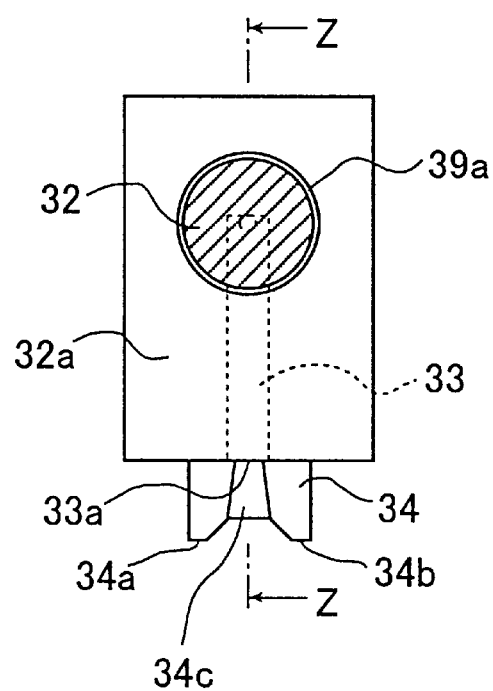
Figure 20:
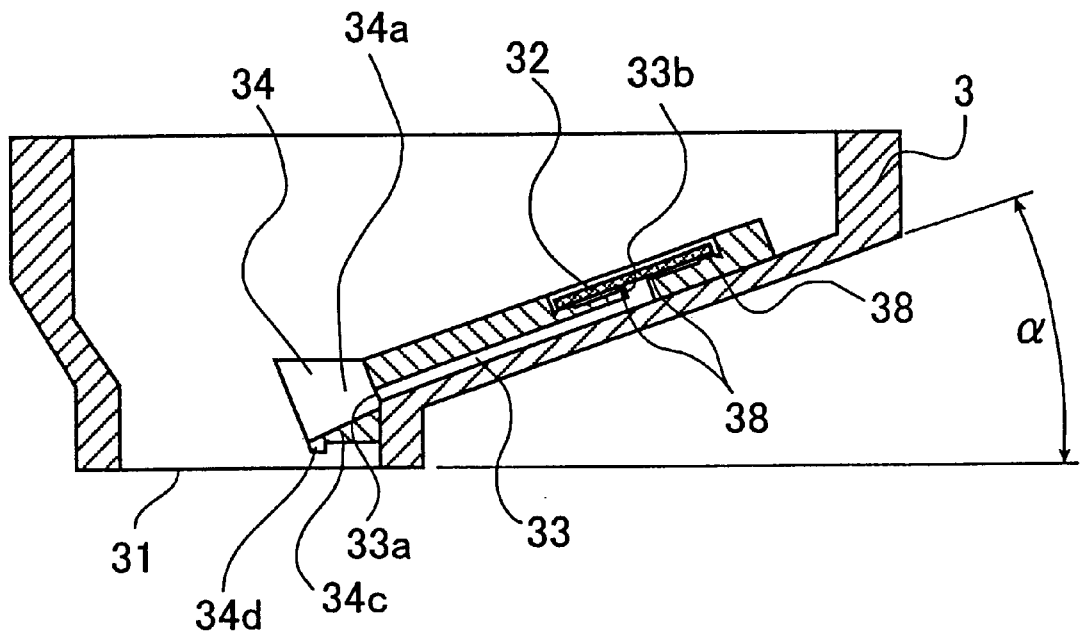
FIG. 20 is a cross sectional view taken along lines Z—Z in FIG. 19.

FIG. 19 is a plan view showing an embodiment of the body fluid inlet 34 which comprises two guide members 34a and 34b and a lower plate member 34c covering three directions (right, left and downward directions) of the body fluid inlet 33a. FIG. 20 is the cross sectional view taken along lines Z—Z of FIG. 19. In the preferred embodiment, the structure including the lower plate member 34c as shown in the figures is enable to prevent the air from ingressing into the body fluid, even if the air flow may slightly occur through a gap space between the bottom surface of the opening 31 and the skin surface when the suction means within the body fluid-monitoring system 9 was applied. The distal ends of the side guide members 34a and 34b may be mounted at an angle less than 90° to the bottom surface of said second housing 3. Furthermore, the structure including the projection 34d on the lower side of the distal end of the guide 34, especially on the lower plate member 34c, can limit the volume of the body fluid to the volume within the above gap space introduced by capillary action.

When the body fluid is collected by the system as described above, the puncture needle 41 passes near the tip of the body fluid guide 34 or between said body fluid guide members before puncturing the skin. When the skin is punctured with the puncture needle 41 and the body fluid droplet of required volume is formed, the droplet contacts the body fluid guide 34. The body fluid is then guided into the flow path 33, and to the test strip 32. Preferably, the distance between the course of the puncture needle 41 and the tip of the body fluid guide 4 is about 3 mm at most, and more preferably, up to about 1 mm in view of the volume of the body fluid required for the measurement. When the body fluid guide 34 is of the type comprising the guide members 34a and 34b as shown in the figures, the puncture needle 41 may pass between the guide members 34a and 34b.

The bottom surface 3a of the second housing 3 should play the role of guiding the second opening 31 forming the distal opening 5 to the site to be lanced (for example, on the finger tip or belly). For such purpose, the surface 3a is preferably tapered at an angle α from the second opening 31. Since the bottom surface 3a is tapered as described above, the part in contact with the skin will be only the distal opening 5 and not all the areas surrounding the distal opening 5. As a consequence, the user can feel the position of the distal opening 5, and identify the lancing site on the skin by the feeling. The tapering angle α is preferably at least 10 degrees. The embodiment shown in FIG. 6 has the tapering angle α in the range of 10 to 45 degrees. Also encompassed in the invention is an embodiment wherein the bottom surface 3a is not tapered at an angle α, and instead, the second opening 31 protrudes from the main body of the second housing 3.

It should be noted that, when the bottom surface 3a of the second housing 3 is tapered at an angle α, the test strip housing 32a is also tapered at the same angle in relation to the body fluid guide 34.

The method for fixedly securing the first housing 2 with the second housing 3 is not particularly limited. In an embodiment, the first housing 2 is secured to the second housing 3 so that the sleeve 21 of the first housing 2 rests on the shoulder 3b of the second housing 3, and the engagement means 24a and 24b of the first housing 2 is engaged to the engagement means 35a and 35b of the second housing 3. Alternatively, the first housing 2 and the second housing 3 are secured by bonding the contact surfaces with an addhesive or by fusion. Such structure enables the user to mount the first housing 2 and the second housing 3 at once as an assembly 1 and eliminates the user from the need of separately mounting the first housing 2 and the second housing 3 to the body fluid-monitoring system 9 (see FIG. 6). This in turn means that the user can also remove the first housing 2 and the second housing 3 at once as an assembly 1.

Alternatively, the first housing 2 may be pushed and fitted into the second housing 3 as shown in FIG. 7.

It should be noted that, in the embodiment as described above, the test strip housing 32a is formed on the bottom surface 3a. When the second housing 3 has a sleeve which fixedly receive the first housing 2 in its interior, the space required for the second housing 3 will be reduced. Such embodiment will be described later as the second embodiment.

The assembly 1 is preferably sealed in a protective shield 8 after its assembly, namely, after assembling to form the distal opening 5 the first housing 2 having the sealed sleeve 21 and the sterilized puncture needle 41 enclosed therein and the second housing 3 having the body fluid-detecting means. The structure of the protective shield 8 is not limited as long as the assembly 1 of particular embodiment can be sealed in its interior. The embodiment of the protective shield 8 shown in the drawings is the one in the form of a sheet, and the protective shield 8 of this embodiment can be removed immediately before the use by tearing the sheet from the notch 81. The first seal member 6 may be provided with a connector 61 and the connector 61 may be connected to a part of the interior of the protective shield 8, and in such a case, the first seal member 6 may be simultaneously removed from the first opening 22 upon removal of the protective shield 8. Similarly, when the second seal member (not shown) is present, the second seal member may also be connected to the protective shield 8 in its interior, and in such case, both the first seal member 6 and the second seal member will be removed from the first opening 22 and the proximal opening 23, respectively, upon removal of the protective shield 8.

In the embodiment as described above, the protective shield 8 was in the form of a sheet. The protective shield 8 may also comprise a rigid plastic casing. The material used for the protective shield 8 is not limited, and when the protective shield 8 comprises a sheet, the protective shield 8 may be produced from a material the same as the first seal member 6 or the second seal member, and when the protective shield 8 comprises a hard plastic case, it may comprise a material the same as the first housing 2 or the second housing 3.

The present invention provides a body fluid-monitoring system comprising a main body of the body fluid-monitoring system and the assembly as describe above. In this body fluid-monitoring system, the main body includes a lancing means for advancing and retracting the lancet, a means for measuring the target component in the body fluid, and a means for detachably holding the assembled housings of the assembly. The assembly is held in the main body by the holder means, and the connector of the lancet is fitted into a recess formed in the distal end of the lancing means.

Next, the operation of the assembly 1 is described by referring to FIG. 6 and FIGS. 21 to 23.

In the case wherein the assembly 1 is sealed in the protective shield 8, when the protective shield 8 is removed from the assembly 1, the first seal member 6 (and the second seal member, if present) will be removed simultaneously with the protective shield 8. Next, the assembly 1 is mounted to the distal end of the body fluid-monitoring system 9. The connector 42 of the lancet 4 then fits into the recess 92 formed in the distal end of the lancing means 91, and a spring 94 connected to the lancing means 91 is thereby compressed. It should be noted that a member such as an O ring 95 is preferably provided at the distal end of the body fluid-monitoring system 9 to enable reliable and gas-tight fixture of the assembly 1 to the distal end of the body fluid-monitoring system 9. The system is now ready for use in the measurement.

Figure 21:
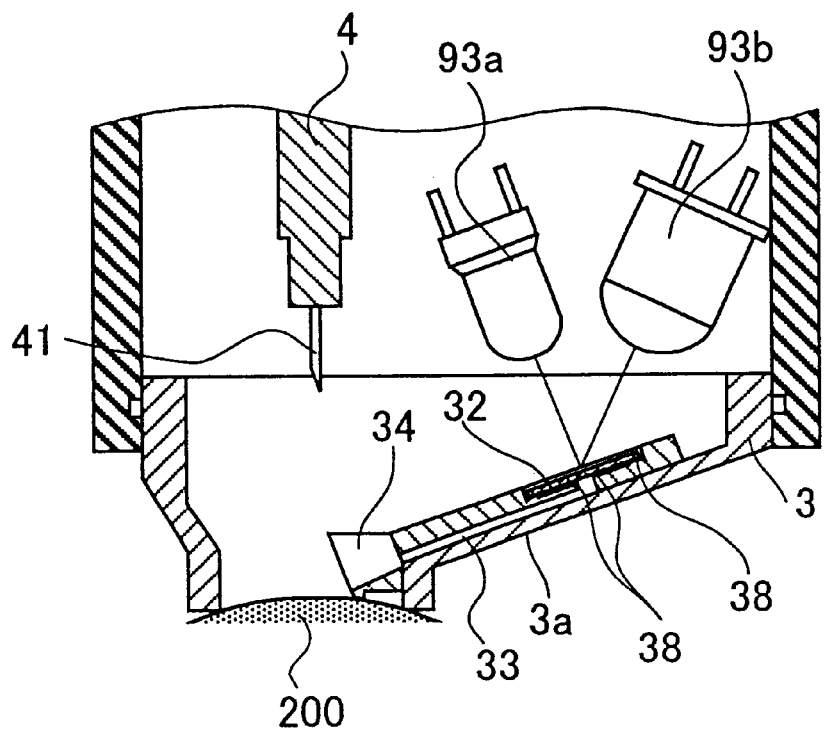
FIG. 21 is a schematic view for explaining the operation of the assembly 1 according to the present invention.
Figure 22:
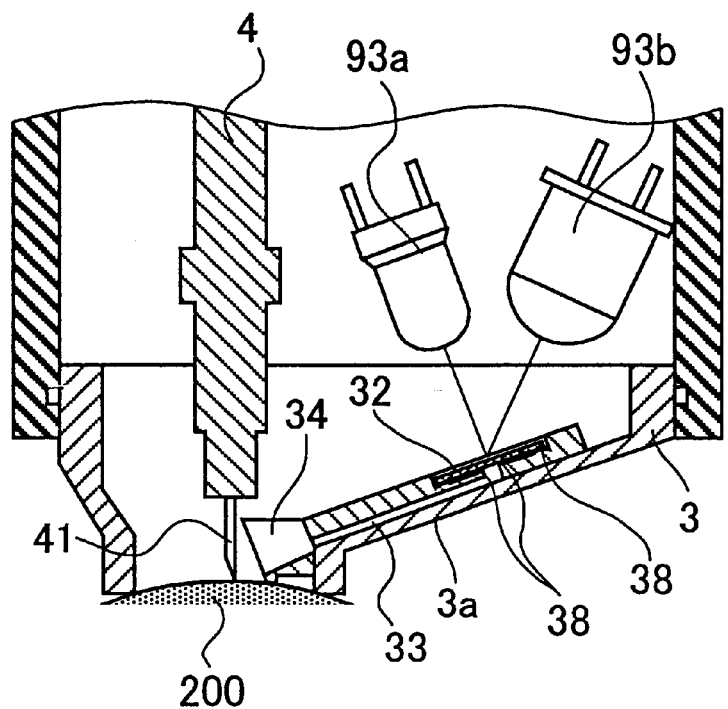
FIG. 22 is a schematic view for explaining the operation of the assembly 1 according to the present invention.

In the measurement, the body fluid-monitoring system 9 is pressed against the skin 200 with the distal opening 5 of the assembly 1 positioned at the lancing site (see FIG. 21). Compression of the spring 94 is then released by a button 96 to urge the lancing means 91 toward its distal end. The lancing means 91 then pushes the lancet 4, and the puncture needle 41 is thereby pressed into the skin 200 (see FIG. 22). After the puncture, the needle 41 is pulled back into the assembly to be accommodated therein by the recovery of the spring 94 to its original length or by means of a different spring (not shown). The body fluid-monitoring system 9 at this point is shown in FIG. 6.

The body fluid-monitoring system 9 may also have a suction means. The suction means is not limited to any particular type as long as it is capable of reducing the pressure in the interior of the main body housing upon pressing of the opening 5 against the lancing site. Typical suction mechanisms are electric and manual pumps.

Figure 23:
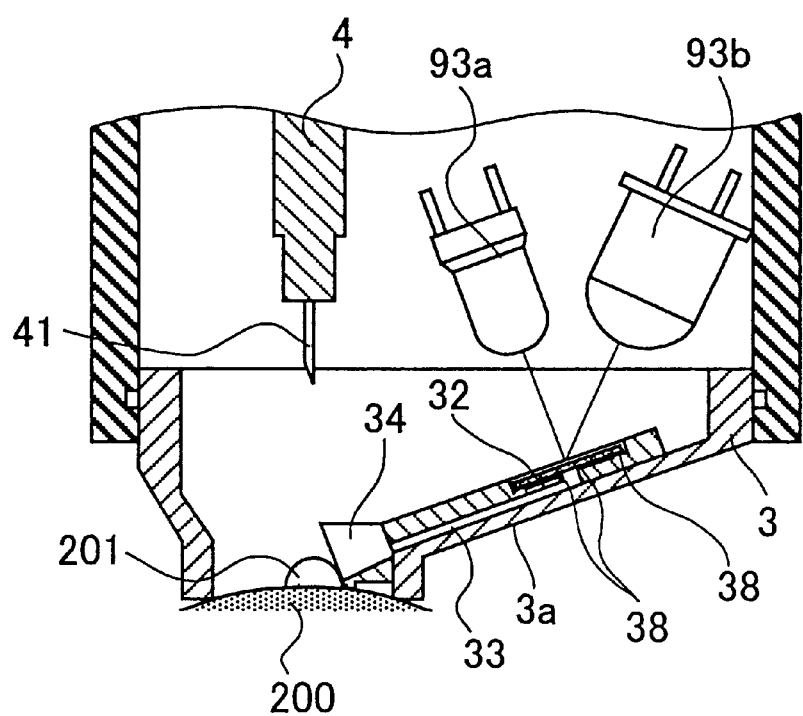
FIG. 23 is a schematic view for explaining the operation of the assembly 1 according to the present invention.

When the body fluid (blood) appears from the lanced site after the lancing, the body fluid is introduced from the body fluid guide 34 into the flow path 33, and to the test strip 32 (see FIG. 23). The body fluid that has reached the test strip 32 reacts with the reagents immobilized therein to undergo the color reaction. The color developed at the test strip 32 is measured for the absorption (or emission) by the optical elements (light emitting device 93*a* or light receiving device 93*b*) in the body fluid-measuring means 93 for calculation of the level of the target component. After completing the series of operation, the assembly 1 is detached from the distal end of the body fluid-monitoring system 9. The lancet 4 accommodated in the assembly 1 will be simultaneously removed from the system 9.

It should be noted that the body fluid-measuring means 93 of the body fluid-monitoring system 9 is not limited to the optical means as mentioned above, and the assembly 1 should be provided with the body fluid detection means 32 of the type corresponding to the type of the body fluid-measuring means 93. In other words, the body fluid detection means 32 is not limited to the test strip. A typical combination of the body fluid detection means 32 and the body fluid-measuring means 93 is an electrode and a processor for converting the measured current data into the blood glucose value.

In the assembly of the present invention as described above, the second housing may be the one wherein an opening is defined in its body portion; a sleeve is provided in its interior to fittingly receive at least a part of the sleeve of the first housing; and the detection area of the body detection means is arranged on the exterior surface of the sleeve of the second housing. When such structure is adopted, the space required for the body fluid detection means will be reduced, and the size of the assembly can be minimized.

Next, the second embodiment of the present invention having a second housing of such structure is described by referring to FIGS. 7 to 12.

FIG. 7 is a cross sectional view of an assembly 101 according to the second embodiment of the present invention.

The assembly 101 comprises a first housing 102 and a second housing 103. As shown in the cross sectional view of FIG. 8, the first housing 102 has a sleeve 121 wherein a lancet 104 is movably accommodated. The sleeve 121 has a first opening 122 at its distal end and a proximal opening 123 at its proximal end.

Figure 9:
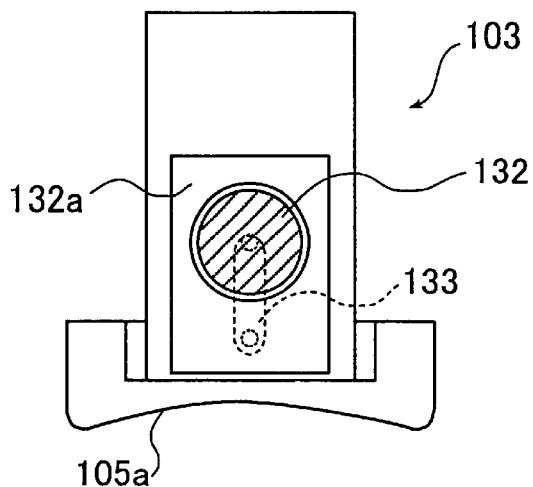
FIG. 9 is a front view of the second housing 103.
Figure 10:
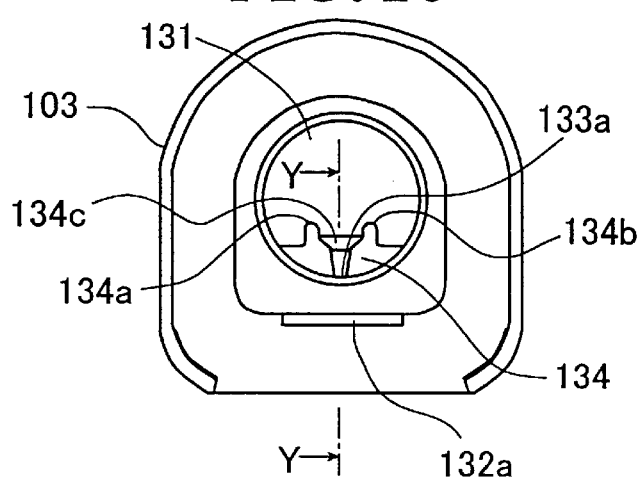
FIG. 10 is a top view of the second housing 103.

As shown in the front view of FIG. 9 and the top view of FIG. 10, the second housing 103 has a second opening 131, and a detection means (a test strip) 132 is provided in the second housing 102.

The first housing 102 and the second housing 103 are fixedly secured to each other to constitute the assembly 101 such that the first opening 122 and the second opening 131 surrounding the first opening 122 together form the distal opening 105. The first housing 102 is fixedly secured to the second housing 103 by firmly fitting the first housing 102 in the second housing 103. The contact surfaces of the first housing 102 and the second housing 103 may be adhered or fused with each other, and alternatively, an engagement means may be provided on both of the first housing 102 and the second housing 103 for engagement therebetween by fitting. Such structure enables the user to mount the first housing 102 and the second housing 103 at once as an assembly 101 and eliminates the user from the need of separately mounting the first housing 102 and the second housing 103 to the body fluid-monitoring system. (The body fluid-monitoring system is not shown. An equivalent body fluid-monitoring system, however, is shown in FIG. 6 as the body fluid-monitoring system 9. In the following description, FIG. 6 may be referred for the explanation of the body fluid-monitoring system.) This in turn means that the user can also remove the first housing 102 and the second housing 103 at once as an assembly 101.

As described above, the first housing 102 has the sleeve 121 in its interior, and the lancet 104 is movably accommodated in the sleeve 121. The sleeve 121 is not limited for its shape, and it may be either a cylinder or a rectangular tube. For structural easiness of production, the sleeve 121 is preferably a cylinder.

The lancet 104 has a puncture needle 141 at the distal end, and a connector 142 at the proximal end for connection with the lancing means (not shown but equivalent to the lancing means 91 of the first embodiment) in the body fluid-monitoring system. The shape of the connector 142 is not limited to the convex type as shown in the drawings, and the connector 142 of any shape may be employed as long as it corresponds to the shape of the lancing means. In addition, the connector 142 may not necessary extend beyond the proximal opening 123.

The lancet 104 is secured at a position near the proximal end of the sleeve 121, namely, at a position such that the puncture needle 141 does not extend beyond the first opening 122. The lancet 104 is secured to the sleeve 121 at a firmness such that the puncture needle 141 does not extend beyond the first opening 122 before the use, such that that the operation of connecting the connector 142 with the lancing means can be accomplished, and such that the connector 142 is released from the secured position when the lancet 104 is urged by the pushing force of the lancing means upon its use. The means for securing the lancet 104 is not limited, and the lancet 104 may be secured by providing an engagement means on the interior surface of the sleeve 121 and/or on the exterior surface of the lancet 104; by utilizing the friction between the interior surface of the sleeve 121 and the exterior surface of the lancet 104; or by weakly bonding the contact surfaces with an adhesive or by fusion.

When the proximal opening 123 is not sealed with the second seal member as will be described layer, the lancet 104 before its use is secured at a position near the proximal opening 123 such that the proximal opening 123 is sealed by the lancet 104. Such sealing of the proximal opening 123 may be accomplished by the same method as described for the securing of the lancet 104, and in a typical embodiment, the lancet 104 is fitted into the space defined by a ridge 125 extending in circumferential direction on the interior surface of the sleeve 121 as shown in FIG. 7. Alternatively, the interior of the sleeve 121 may be narrowed near its proximal end and the lancet 104 may be fitted into the narrow proximal end of the sleeve 121, or the lancet 104 may be fitted into the space between protrusions provided in some part of the interior surface of the sleeve 121 to facilitate gas-tight contact between the interior surface of the sleeve 121 near its proximal end and the exterior surface of the lancet 104 near its proximal end.

When the assembly 101 is detached from the body fluid-monitoring system, the lancet 104 which is connected to the lancing means of the body fluid-monitoring system through the connector 142 will be pulled back toward the proximal end of the first housing 102. When the lancet 104 is fittingly secured in the securing/sealing means as described above such as the ridge 125 extending in circumferential direction, the connector 142 becomes detached from the lancing means, and the assembly 101 can be finally detached from the body fluid-monitoring system. In the course of the detachment, the puncture needle 141 becomes firmly secured in the sleeve 121, and the puncture needle 141 is reliably prevented from extending beyond the second opening 131. Accidental prickling of the skin by the puncture needle 141 after its use is thereby prevented.

Since the lancet 104 must fit in the sleeve 121 near its proximal end to seal the proximal opening 123, the lancet 104 should have a cross section which corresponds to the cross section of the sleeve 121. In principle, the lancet 104 may be formed from the same material as the first housing 102 or the second housing 103 as will be described below, and the material used for the lancet 104 may preferably have some flexibility.

The interior of the first housing 102 is maintained in sterilized condition by sterilizing the sleeve 121 after enclosing the lancet 104 in its interior and sealing the proximal opening 123; or enclosing the sterilized lancet 104 in the interior of the sterilized sleeve 121 and maintaining the interior of the sleeve 121 in sealed conditions until its use. Of these procedures, sterilization of the sleeve 121 after enclosing the lancet 104 and sealing the proximal opening 123 is advantageous for ease of operation. The sterilization may be conducted by any method, for example, by sterilization with EOG, γ ray, electron beam, or the like. As described above, the first housing 102 is assembled with the second housing 103 to produce the assembly 101 after ensuring that the sterility of the interior of the sleeve 121 will be maintained until its use.

Exemplary materials used for the first housing 102 include ABS, polyethylene, polypropylene, polystyrene, polyvinyl chloride, polyvinylidene chloride resin, polyphenylene oxide, thermoplastic polyurethane, polymethylene methacrylate, polyoxyethylene, fluororesin, polycarbonate, polyamide, acetal resin, acryl resin, polyethylene phthalate and other thermoplastic resins used in the injection molding; and phenol resin, epoxy resin, silicone resin, unsaturated polyester resin and other thermosetting resins.

The interior of the sleeve 121 is kept in gas-tightly sealed conditions by sealing the first opening 122 and the proximal opening 123. The first opening 122 is sealed by the first seal member 106. As shown in the drawings, the first seal member 106 is in the form of a plug fitted and secured in the first opening 122 to gas-tightly seal the interior of the sleeve 121. It should be noted that the first seal member 106 may also be in the form of a lid or a plug for ease of bonding by adhesion or fusion as well as peeling. Although it is preferable that the proximal opening 123 is gas-tightly sealed by fittingly securing the lancet 104 as described above, the proximal opening 123 may also be sealed with a second seal member (not shown) similar to the first seal member 106.

The second housing 103 has the second opening 131, and a detection means (a test strip) 132 is provided in the second housing 102. In the second embodiment, the test strip 132 is provided such that the plane of the test strip 132 is substantially parallel to the axial direction of the sleeve 121 when the first housing 102 and the second housing 103 are assembled into the assembly 101. In such structure, the test strip 132 is secured to the exterior surface of the sleeve 121. In the present embodiment, the test strip 132 placed in a test strip housing 132a is secured to the second housing 103. It should be noted that the body fluid detection means is not limited to the test strip, and any medium suitable as a body fluid detection means of the body fluid monitoring system may be used.

The material used for the second housing 103 may be the same as those described for the first housing 102. When the body fluid-measuring means in the body fluid monitoring system is an optical means which conducts the measurement by detecting the color reaction on the test strip, the housing 103 may preferably comprise a non-transparent material to thereby shut out the influence of exterior light and increase the measurement accuracy. For ease of confirming the movement of the body fluid in the flow path 133, the second housing 103 may comprise a colored, translucent resin.

Figure 12:
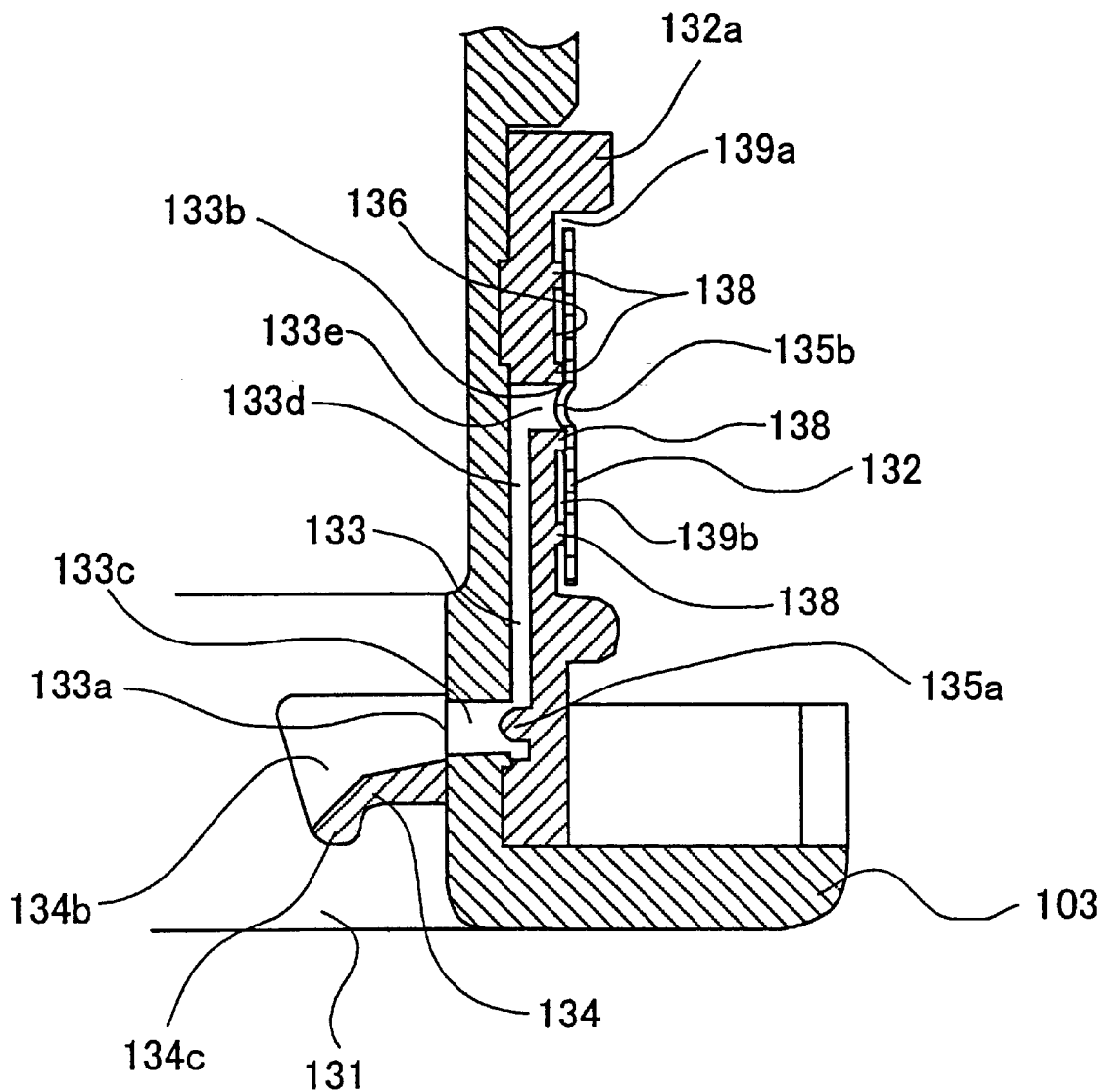
FIG. 12 is a cross sectional view taken along lines Y—Y of the second housing 103 in FIG. 10.

In this embodiment, a body fluid inlet 133a and a flow path 133 for introducing the body fluid from the body fluid inlet 133a to the test strip 132 by capillary action are formed in the periphery of the second opening 131. FIG. 12 is an enlarged cross sectional view of the second housing 103 of the second embodiment taken along lines Y—Y of FIG. 10. As shown in FIG. 12, the flow path 133 is formed from flow path sections 133c, 133d, and 133e intersecting with each other at an angle. More specifically, the flow path section 133c extends from the body fluid inlet 133a, and the flow path section 133d rises upward from the flow path section 133c along the axis of the second housing 103, and the flow path section 133e extends from the flow path section 133d toward the test strip 132. In this embodiment, the flow path 133 is formed as a gap when the test strip housing 132a is assembled to the second housing 103.

The cross section and the length of the flow path 133 may vary in accordance with the amount of the body fluid required for the measurement. The flow path 133, however, is preferably designed such that the volume of the body fluid remaining in the flow path 133 is minimized. The flow path 133 may typically comprise a groove having a semi-circular, V-shaped, or rectangular cross section, and for reducing the amount of the body fluid remaining in the flow path 133, the flow path 133 may preferably comprise a shallow groove having a rectangular cross section. The depth is preferably in the range of about 0.05 to about 0.5 mm, and the width is preferably in the range of from about 0.5 to about 3 mm. The flow path 133 may preferably have a short length although the length may depend on the position of the body fluid-measuring means of the body fluid monitoring system. The suitable length, however, is in the range of from about 5 mm to about 15 mm.

Figure 11:
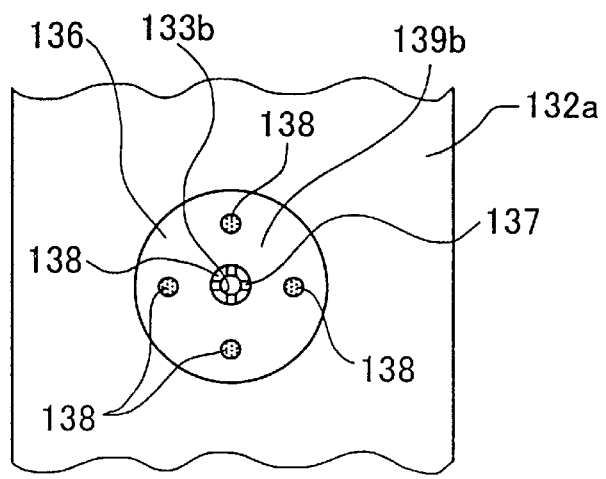
FIG. 11 is a front view of the test strip holder 136 (without paper) in the second housing 103.

When the body fluid is introduced along the flow path 133 from the body fluid inlet 133a to the test strip 132 in a closed system, the capillary action may stop before the reaching of the body fluid to the test strip 132. In view of such situation, provision of an air vent is necessary, and to be more specific, the test strip holder 136 provided on the exterior surface of the housing 103 as a recess is formed to a structure as shown in FIG. 11 in its plan view. In this structure, the test strip supports 138 and the air vent 137 at the end 133*b* of the flow path 133 on the side of the test strip 132 are formed so that the test strip 132 can be secured as shown in FIG. 12 wherein a gap 139*a* is defined between the periphery of the test strip 132 and the periphery of the test strip holder 136, and a gap 139*b* is defined between the lower surface of the test strip 132 and the test strip holder 36. The test strip 132 is supported between the test strip supports 138 and the end 133*b* of the flow path 133.

As shown in FIG. 12, in the case of the flow path 133 in the second embodiment of the present invention, the flow path section 133*c* extending from the body fluid inlet 133*a* intersects at an angle with the flow path section 133*d* extending along the axis of the second housing 103, and the flow path section 133*d* intersects at an angle with the flow path section 133*e* extending toward the test strip 132. When the fluid of high viscosity as in the case of the body fluid flows along the flow path of such configuration, meniscus is likely to be formed at the front end of the liquid flow due to the surface tension. In view of such situation, in the flow path 133 of this embodiment, a projection extending into the flow path 133 is preferably formed at each corner of the flow path 133 so that the fluid forming the meniscus may contact the projection as the fluid advances through the flow path. To be more specific, a projection 135*a* extending into the flow path section 133*c* is formed at the corner defined between the flow path sections 133*c* and 133*d*, and a projection 135*b* extending into the flow path section 133*b* is formed in the test strip 132. The projections 135*a* and 135*b* will release the surface tension responsible for the meniscus formation.

It should be noted that meniscus is a phenomenon that occurs in a tube and that becomes evident when the advance of the liquid through the tube is terminated by the action of surface tension, and a concave or convex surface is formed on the liquid surface. When the tube is wetted by the liquid, the meniscus formed is a concave meniscus and the liquid surface will be lifted along the tube interior surface. Meniscus formation is most likely to occur at or near the corner of a capillary.

The flow path 133 may be formed from the same material as the second housing 103. The flow path 133, however, is preferably formed from a material having a high hydrophilicity such as acryl resin. When the material is not sufficiently hydrophilic, the surface of the flow path 133 may be treated to impart the surface with the hydrophilicity to improve the sucking of the body fluid into the flow path 133. Typical such treatments include physical activations such as ozone treatment, plasma treatment, glow discharge, corona discharge, UV irradiation; coating of a surfactant, water soluble silicone, hydroxypropyl cellulose, polyethylene glycol, polypropylene glycol, or the like.

The body fluid inlet 133*a* is preferably formed with a body fluid guide 134 on its periphery. The body fluid guide 134 has the function of guiding the body fluid which becomes in contact with the guide 134 to the body fluid inlet 133*a*. The body fluid guide 134 may be formed from the same material as the second housing 103 or the flow path 133, and the body fluid guide 134 is preferably imparted with hydrophilicity as in the case of the flow path 133. The body fluid guide 134 should have a structure which is capable of rapidly guiding the body fluid to the body fluid inlet 133*a*, and which is capable of retaining a large amount of the body fluid to prevent the spreading or flowing out of the body fluid to surrounding areas. When the body fluid guide 134 has an inappropriate shape, the excess body fluid that was not sucked from the body fluid inlet 133*a* will spread around the second opening 131 to induce sanitary problem. The body fluid guide 134 of an inappropriate shape will also result in an insufficient sucking of the body fluid into the flow path 133, and the amount of body fluid required for the measurement will be increased to result in the increased burden of the patient. A typical body fluid guide 134 comprises guide members 134*a* and 134*b* in the form of rails provided on the periphery and on opposite sides (on the right and left) of the body fluid inlet 133*a*. It should be noted that the opposed interior surfaces of guide members 134*a* and 134*b* may be either parallel to each other or unparallel such that the space defined between the opposed interior surfaces widen toward the center of the body fluid droplet. The latter structure is more preferable since the suction of the body fluid is more reliably and more rapidly conducted. The body fluid guides 134 may be the one further comprising a guide member 134*c* covering the lower direction of the body fluid inlet 133*a*. The body fluid guides 134 of other embodiments are also acceptable, and the body fluid guide 134 may be the one wherein the body fluid inlet 133*a* is covered in all four directions (right, left, upward and downward directions).

The body fluid guide 134 may preferably define an interior space with a width of about 1 mm to about 3 mm, a height of about 0.5 mm to about 3 mm, and a length of about 1 mm to about 3 mm since the body fluid in an amount of about 4 $\mu$l forms a droplet having a diameter of about 3 mm and the guide 134 may preferably define a space equivalent to the maximum required volume of the body fluid. The height of the guide 134*a* and 134*b* is preferably equivalent to the maximum diameter of the body fluid inlet 133*a*.

In the lancing, the puncture needle 141 passes near the tip of the body fluid guide 134 or between said body fluid guide members before puncturing the skin. When the skin is punctured with the puncture needle 141 and the body fluid droplet of required volume is formed, the droplet contacts the body fluid guide 134. The body fluid is then guided into the flow path 133, and to the test strip 132. Preferably, the distance between the course of the puncture needle 141 and the tip of the body fluid guide 134 is about 3 mm at most, and more preferably, up to about 1 mm in view of the volume of the body fluid required for the measurement.

The surface of the second housing 103 near the second opening 131 may be formed as a curved surface 105*a* with a curve corresponding to the lancing site. The curved surface 105*a* will then play the role of guiding the distal opening 105 to the lancing site (for example, on the finger tip or belly). In the embodiment shown in FIG. 9, the second housing 103 is formed with the curved surface 105*a* having a curve corresponding to the finger, and the recessed area of the curved surface 105*a* facilitates positioning of the distal opening 105 to the lancing site on the finger.

The body fluid detecting means or the test strip 132 is not limited to any particular type, and any material matching with the body fluid-measuring means of the body fluid monitoring system may be used. For example, when the body fluid-measuring means is an optical measurement means which detects color reaction in the test strip as in the case of the measurement of glucose in blood, the test strip 132 may be impregnated with glucose oxidase, peroxidase, and a chromogenic agent followed by drying. The test strip 132 is preferably a porous membrane in the form of a nonwoven fabric, a woven fabric, a stretched sheet, or the like prepared from a material such as a polyester, a polyamide, a polyolefin, a polysulfone, a cellulose, or the like. Since the test strip 132 is impregnated with various reagents as well as the body fluid, the test strip 132 is preferably the one formed from a hydrophilic material or the one which has been treated to impart hydrophilicity. The test strip 132 may be either a mono-layer sheet or a multi-layer sheet. When the test sheet 132 comprises a multi-layer sheet, the layers should be densely stacked on one another as shown in the drawings.

When the first housing 102 wherein at least the puncture needle 141 is enclosed in sterilized state by maintaining the seal of the sleeve 121 as described above and the second housing 103 having the body fluid detection means are fixedly secured to each other to form the assembly 101 having the distal opening 105, the whole assembly 101 is preferably sealed in a protective shield 108. The structure of the protective shield 108 is not limited as long as components of the assembly 101 can be sealed in its interior. The embodiment of the protective shield 108 shown in the drawings is the one in the form of a sheet, and the protective shield 108 of this embodiment can be removed immediately before the use by tearing the sheet from the notch 181. If the first seal member 106 is provided with a connector 161, and the connector 161 is connected to a part of the interior of the protective shield 108, the first seal member 106 may be simultaneously removed from the first opening 122 upon removal of the protective shield 108. Similarly, when the second seal member is present, the second seal member may also be connected to the protective shield 108 in its interior, and in such case, both the first seal member 106 and the second seal member will be removed from the first opening 122 and the proximal opening 123, respectively, upon removal of the protective shield 108.

The protective shield 108 is not limited to the one in the form of a sheet, and may comprise a rigid plastic casing. The material used for the protective shield 108 is not limited to any particular type, and when the protective shield 108 is in the form of a sheet, the material used may be those used for the first seal member 106 or the second seal member such as a film coated with aluminum, and when the protective shield 108 comprises a rigid plastic casing, the material used may be those used for the first housing 102 or the second housing 103.

The assembly 101 according to the second embodiment can be used substantially as in the case of the assembly 101 according to the first embodiment of the present invention.

BENEFITS OF THE INVENTION

The present invention provides an assembly for use with a body fluid-monitoring system wherein the lancet (the puncture needle) has been sterilized and the sterilized condition is maintained until its use while adverse effects caused by the sterilization of the lancet such as the adverse effects which might be induced in the reagents impregnated in the test strip are avoided. Use of the assembly according to the present invention ensures safe measurement due to the sterilized conditions maintained until the use of the lancet and simple and reliable attachment and detachment of the lancet and test paper units since both units can be simultaneously handled.

The body fluid-collecting and detecting unit of the present invention has a body fluid guide which enables efficient introduction of the body fluid into its interior, and the measurement can be accomplished by lancing and collecting minimum amount of the body fluid. Therefore, milking and massaging of the lanced site is no longer necessary.

What is claimed is:

1. An assembly having a lancet and body fluid collection and detection means for collecting and detecting a body fluid wherein said assembly is to be detachably mounted on a body fluid-monitoring system having a lancing means and said assembly comprises:

a lancet section comprising
a lancet having a puncture needle on a distal end of the lancet and a connector on a proximal end of the lancet for connection to said lancing means of the body fluid-monitoring system, and a first housing having a sleeve which movably accommodates said lancet in an interior of the sleeve, and which has a first opening on a distal end of the sleeve to enable projection of the needle into an exterior of the sleeve and the proximal opening to enable connection of said connector with said lancing means of the body fluid-monitoring system, and
wherein said lancet before the lancing is secured in said sleeve at a position near the proximal opening to gas-tightly seal said sleeve;

a body fluid-collecting and detecting section comprising the body fluid detection means and a second housing having a second opening for introducing the body fluid into said detection means;

a first seal member for sealing said first opening; and wherein said first housing is gas-tightly sealed with both said first seal member for sealing said first opening and said lancet for sealing said proximal opening; and said first housing and said second housing are fixedly integrated with each other such that said first opening of said first housing and said second opening of said second housing together define a distal opening to enable the projection of said puncture needle to the exterior of said assembly, and the assembly comprised of the lancet section and the body fluid-collection and detection section being a one-piece assembly.

2. An assembly according to claim 1 produced by sterilizing said lancet section having said puncture needle accommodated in said first housing with said first opening and said proximal opening sealed; and assembling the sterilized lancet section with said body fluid-collecting and detecting section to constitute a one-piece assembly.

3. An assembly according to claim 2 wherein the entire assembly after assembling is covered with a protective shield.

4. An assembly according to claim 2 wherein said puncture needle remains sterilized until said first seal member is removed from said first opening.

5. An assembly according to claim 1 wherein the entire assembly after assembling is covered with a protective shield.

6. An assembly according to claim 5 wherein said first seal member is connected to said protective shield and said first seal member is removed from said first opening simultaneously with removal of said protective shield.

7. An assembly according to claim 1 wherein said first housing has a detachment preventing means for preventing detachment of said lancet after use.

8. An assembly according to claim 7 wherein said detachment-preventing means also serves the function of sealing said proximal opening of said sleeve.

9. An assembly according to claim 1 wherein said second housing is defined with a flow path for guiding the body fluid from said distal opening to said body fluid detection means by capillary action, and an inlet port for guiding said body fluid into said flow path.

10. An assembly according to claim 9 wherein said flow path in the second housing comprises a plurality of flow path sections between which corners are defined at an angle, and a projection having a tip, said projection protruding into the flow path is provided on each corner so that the tip of the projection contacts with meniscus of the body fluid formed at the corner.

11. An assembly according to claim 9 wherein said inlet port has a body fluid guide formed along a periphery of the inlet port.

12. An assembly according to claim 11 wherein said body fluid guide comprises two or more guide members and said guide members are projections formed on the periphery of said inlet port.

13. An assembly according to claim 11 wherein said body fluid guide is located inside of said second opening.

14. An assembly according to claim 11 wherein said body fluid guide has a constitution comprising two side members and a lower plate member.

15. An assembly according to claim 14 wherein said lower plate member has a downwardly extending projection on a distal section thereof.

16. An assembly according to claim 15, said second housing having a bottom face, wherein said body fluid guide members are designed such that a width between said side members increases from the side of said inlet to the side of a distal end, and surface tension of said body fluid is lower in an interior space enclosed with said fluid guide members than in an interior of said flow path, and the distal ends of said side members are mounted at an angle less than 90° to the bottom face of said second housing.

17. An assembly according to claim 11, said body fluid guide having a tip, wherein said puncture needle passes near the tip of said body fluid guide or between side members of said body fluid guide during puncture.

18. An assembly according to claim 1 wherein said second housing has a sleeve in an interior of the second housing to fittingly receive at least a part of the sleeve of the first housing, and said sleeve of the second housing has an opening in a body of the sleeve; and
   a detection area of the body fluid detection means is secured to an exterior surface of said sleeve of the second housing.

19. A body fluid-monitoring system comprising a main body of the body fluid-monitoring system and the assembly of claim 1, wherein said main body includes:
   lancing means having a recess at a distal end,
   means for measuring the target component in the body fluid, and
   holder means for detachably holding the assembled housings of the assembly, and
   said assembly is held by said holder means, and the connector of said lancet is fitted into said recess formed in the distal end of said lancing means.

20. A body fluid-collecting and detecting unit for detecting a target component of a body fluid comprising:
   a housing having a bottom face;
   an inlet port for the body fluid;
   a test strip which enables measurement of the target component in the body fluid;
   a flow path for guiding the body fluid from said inlet port to said test strip by capillary action;
   a body fluid guide formed along the periphery of the inlet port, wherein said body fluid guide comprises two or more side members and a lower plate member, and
   wherein said body fluid guide is designed such that a width between said side members increases from the side of said inlet to the side of a distal end, and surface tension of said body fluid is lower in an interior space enclosed with said guide members than in an interior of said flow path, and the distal ends of said side members are mounted at an angle less than 90° to the bottom face of said housing.

21. An assembly having a lancet and body fluid collection and detection means for collecting and detecting a body fluid wherein said assembly is to be detachably mounted on a body fluid-monitoring system having a lancing means and said assembly comprises:
   a lancet section comprising
      a lancet having a puncture needle on a distal end of the lancet and a connector on a proximal end of the lancet for connection to said lancing means of the body fluid-monitoring system, and a first housing having a sleeve which movably accommodates said lancet in an interior of the sleeve, and which has a first opening on a distal end of the sleeve to enable projection of the needle into an exterior of the sleeve and a proximal opening to enable connection of said connector with said lancing means of the body fluid-monitoring system, and
      wherein said lancet before the lancing is secured in said sleeve at a position near the proximal opening to gas-tightly seal said sleeve;
   a body fluid-collecting and detecting section comprising the body fluid detection means and a second housing having a second opening for introducing the body fluid into said detection means;
   a first seal member for sealing said first opening and a second seal member for sealing said proximal opening; and
   wherein said first housing is gas-tightly sealed with both said first seal member for sealing said first opening and said second seal member for sealing said proximal opening; and said first housing and said second housing are fixedly integrated with each other such that said first opening of said first housing and said second opening of said second housing together define a distal opening to enable the projection of said puncture needle to the exterior of said assembly, the assembly comprised of the lancet section and the body fluid-collecting and detecting section being a one-piece assembly.

* * * * *